United States Patent [19]

Jones

[11] Patent Number: 4,573,342
[45] Date of Patent: Mar. 4, 1986

[54] APPARATUS AND METHOD FOR THE AUTOMATIC POROSITY AND PERMEABILITY TESTING OF MULTIPLE CORE SAMPLES

[75] Inventor: Stanley C. Jones, Littleton, Colo.

[73] Assignee: Marathon Oil Company, Findlay, Ohio

[21] Appl. No.: 651,558

[22] Filed: Sep. 14, 1984

[51] Int. Cl.$^4$ .......................................... G01N 15/08
[52] U.S. Cl. .................................................. 73/38
[58] Field of Search ................. 73/37, 38, 864.23, 41, 73/45.1, 45.2, 45; 422/64, 63; 436/47, 48; 209/909, 914, 919

[56] References Cited

U.S. PATENT DOCUMENTS

| | | | |
|---|---|---|---|
| 966,078 | 8/1910 | Bowman | 73/38 |
| 2,516,188 | 6/1950 | Dietert et al. | 73/38 |
| 2,539,355 | 1/1951 | Reichertz | 73/38 |
| 2,618,151 | 11/1952 | Leas | 73/38 |
| 2,676,485 | 4/1954 | Morgan | 73/38 |
| 2,705,418 | 4/1955 | Reichertz et al. | 73/38 |
| 2,737,804 | 3/1956 | Herzog et al. | 73/38 |
| 2,745,057 | 5/1956 | Dotson | 324/13 |
| 2,821,680 | 1/1958 | Slusser et al. | 73/38 |
| 2,867,116 | 1/1959 | Aronofsky et al. | 73/38 |
| 3,158,020 | 12/1964 | Donaldson | 73/38 |
| 3,199,341 | 8/1965 | Heuer, Jr. et al. | 73/94 |
| 3,839,899 | 10/1974 | McMillen | 73/38 |
| 4,043,407 | 8/1977 | Wilkins | 175/50 |
| 4,083,228 | 4/1978 | Turner | 73/32 R |
| 4,227,397 | 10/1980 | Neri | 73/38 |
| 4,253,327 | 3/1981 | Wiley | 73/38 |
| 4,287,754 | 9/1981 | Heitmann | 73/38 |
| 4,403,501 | 9/1983 | Pezzi | 73/38 |
| 4,430,890 | 2/1984 | Hains | 73/147 |
| 4,447,395 | 5/1984 | Englar et al. | 422/64 |
| 4,454,095 | 6/1984 | Holt | 422/64 |
| 4,476,733 | 10/1984 | Chlosta et al. | 422/63 |
| 4,478,095 | 10/1984 | Bradley et al. | 436/47 |

FOREIGN PATENT DOCUMENTS 153457 11/1963 U.S.S.R. ................. 73/38

OTHER PUBLICATIONS

"A Rapid Accurate Unsteady-State Klinkenberg Permeameter", Stanley C. Jones, Marathon Oil Co., Littleton, CO, Oct., 1972.

Primary Examiner—Stewart J. Levy
Assistant Examiner—Hezron E. Williams
Attorney, Agent, or Firm—Jack L. Hummel; Rodney F. Brown

[57] ABSTRACT

An apparatus automatically determining the permeability and porosity for a plurality of core samples. The apparatus includes a carousel capable of carrying a plurality of core samples, a piston located under the carousel for selectively raising one of the core samples from the carousel into an upper sample holder wherein the piston in cooperation with the sample holder seals the core sample in a test chamber, and a second piston located internal to the first piston for selectively closing and opening the lower end of the core sample so that gas introduced in the upper end of the core sample can be utilized to conduct a permeability test when the lower end is open and a porosity test when the lower end is closed by the internal piston.

36 Claims, 36 Drawing Figures

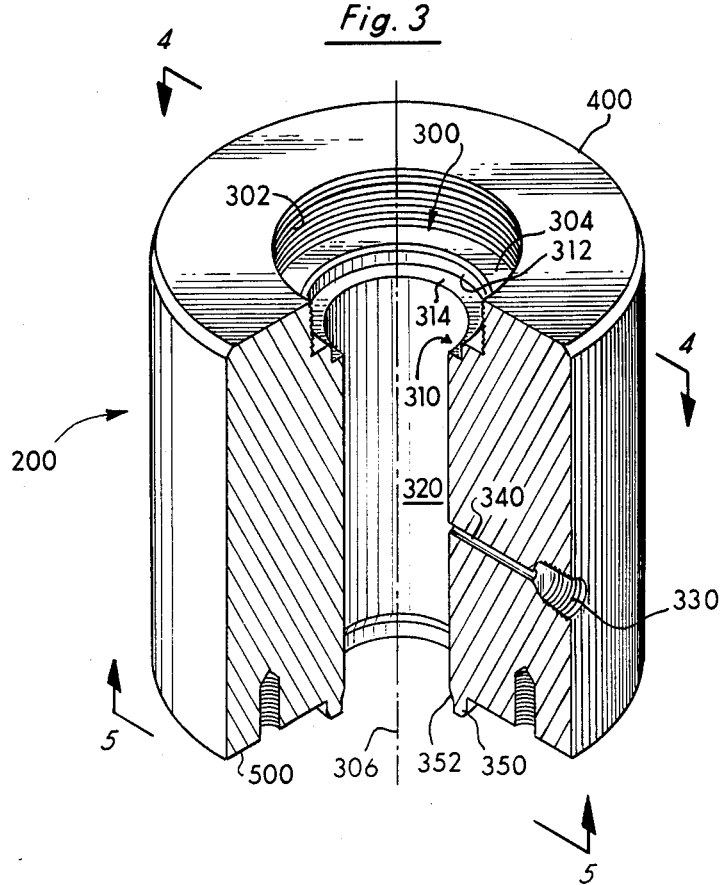
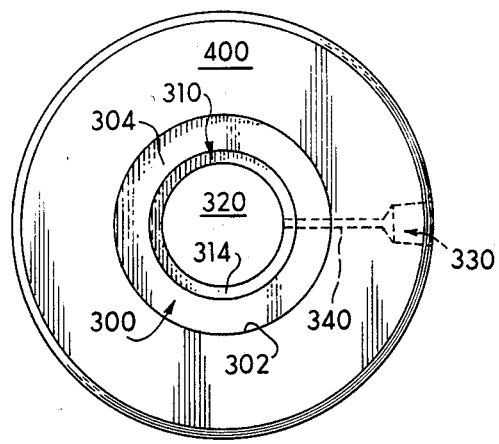 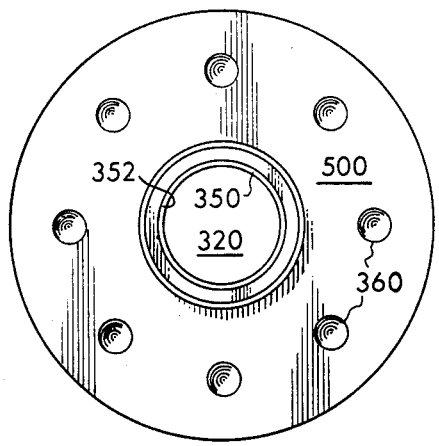

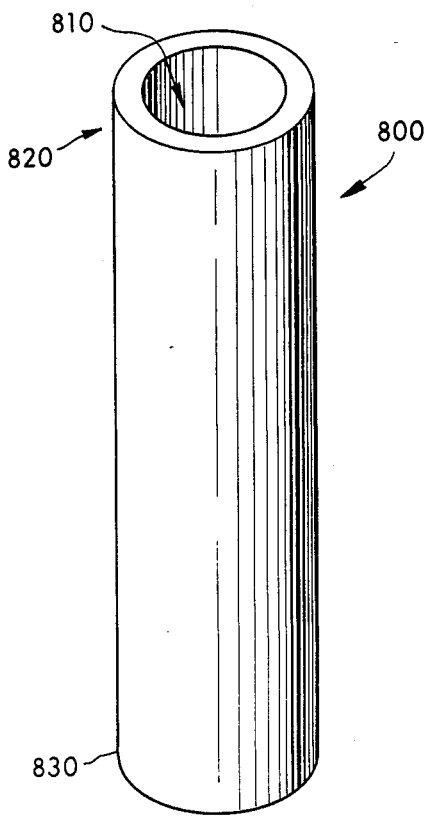
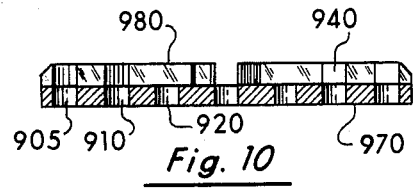
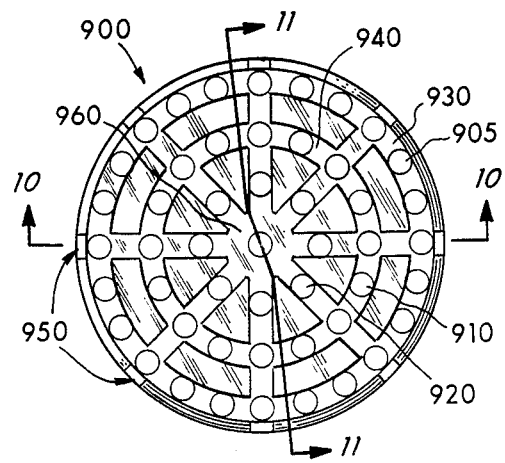
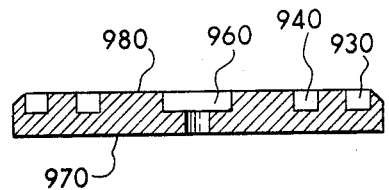

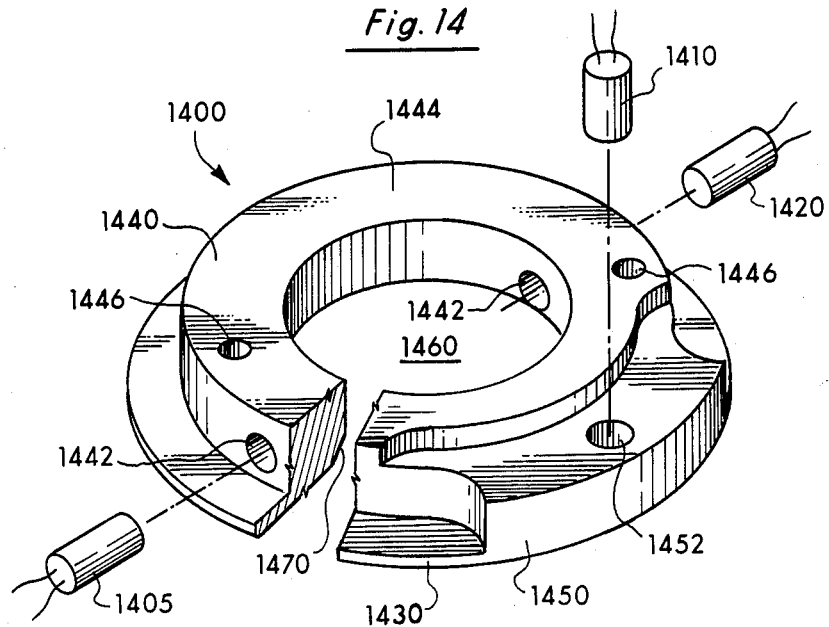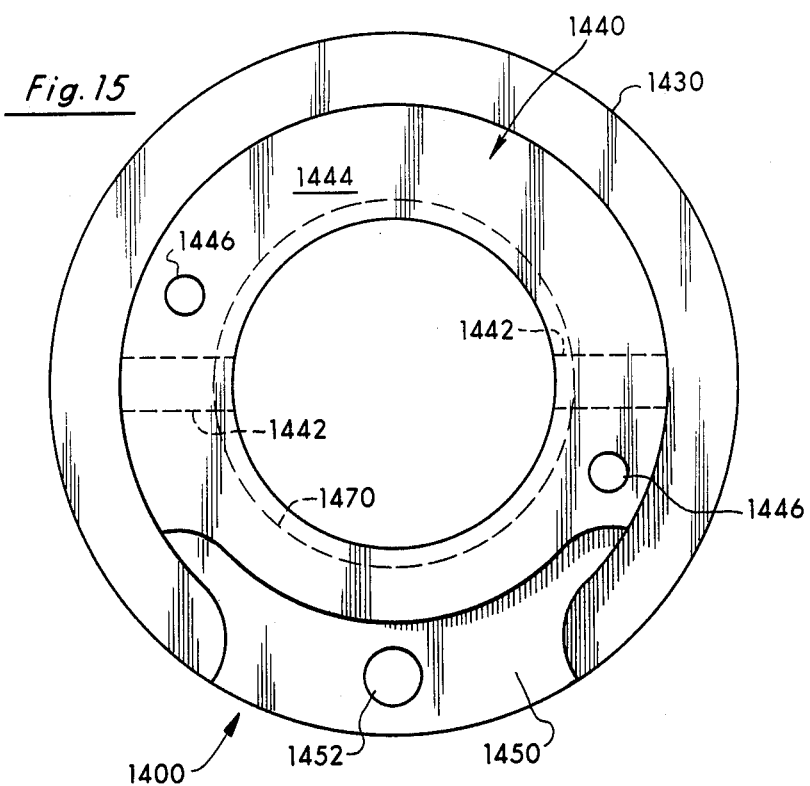

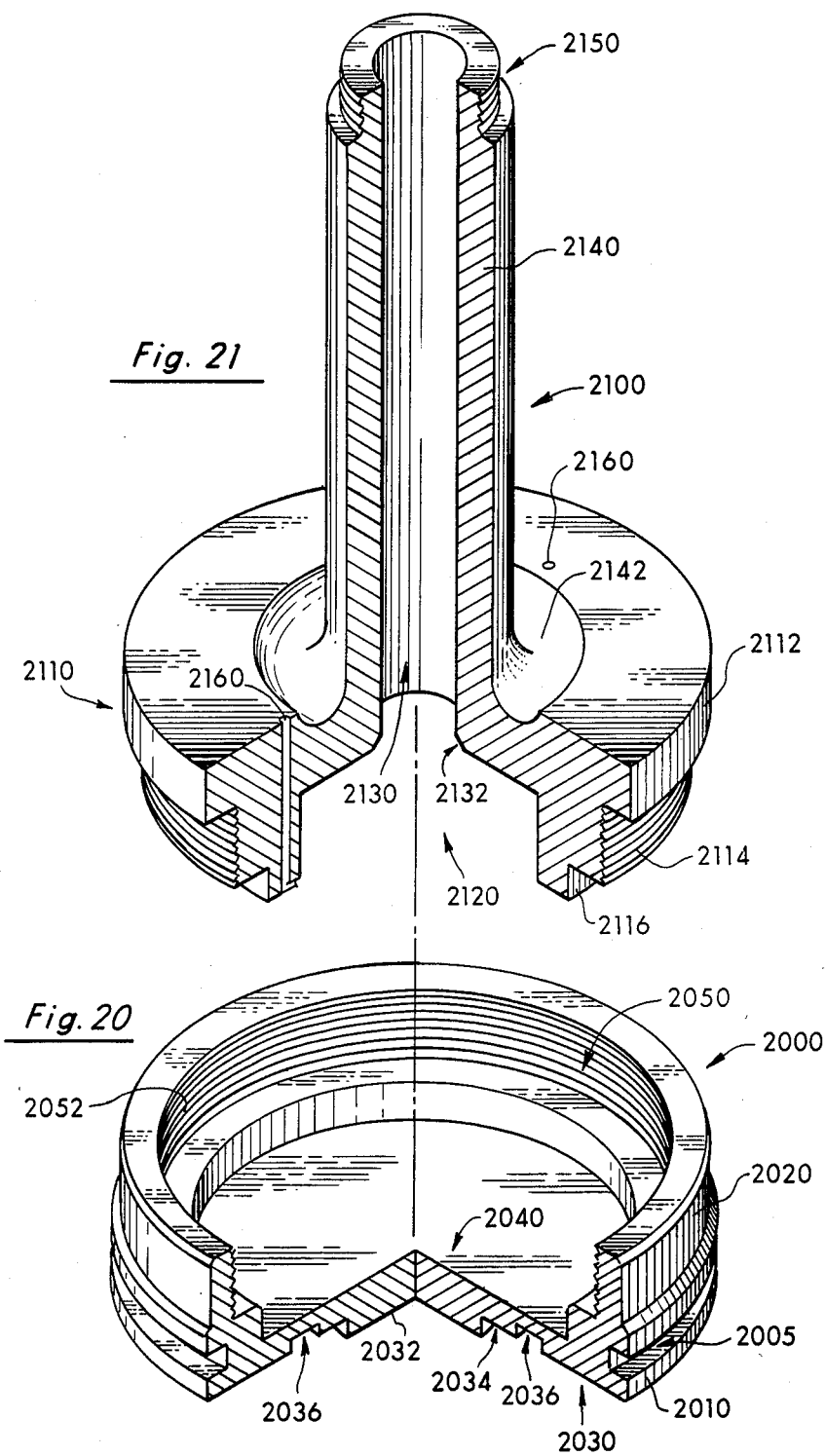

4,573,342

APPARATUS AND METHOD FOR THE AUTOMATIC POROSITY AND PERMEABILITY TESTING OF MULTIPLE CORE SAMPLES

BACKGROUND OF THE ART

1. Related Application

This application is related to "IMPROVED PERFORATED END PLUG PLATE FOR TESTING CORE SAMPLES", Ser. No. 651561 filed concurrently with this application.

2. Field of the Invention

The present invention relates to a method and apparatus for ascertaining the permeability and/or porosity of core samples from an underlying rock formation and, more particularly, to a method and apparatus for automatically testing a number of such core samples.

3. Background of the Art

Two important parameters for evaluating production of an underlying oil or gas bearing formation are the permeability and porosity of core samples actually taken from the formation. A measurement of permeability of the core provides an indication as to how fast the oil or gas will flow from the formation upon production whereas a measurement porosity provides information as to the amount of oil or gas contained within the formation. The determination of both porosity and permeability are based upon complex mathematical determinations and both are common measurements in the oil and gas industry.

An understanding of these mathematical formulas is not necessary for the understanding of the present invention. However, a discussion of the mathematical formulas for determining Klinkenberg permeability, the Klinkenberg slip factor and the Forcheimer tubulence factor observed in core plugs is set forth in the inventor's prior publication entitled "A Rapid Accurate Unsteady-State Klinkenberg Permeameter", *Society of Petroleum Engineers Journal,* October, 1972, Pages 383–397. In that publication, a method and apparatus for performing permeability tests on core samples is set forth. In that disclosure, each sample core is manually loaded into a Hassler core holder and the sleeve contained therein is then pressurized to simulate an overburden pressure. A gas, such as nitrogen, is then introduced into one end of the core and the passage of the gas through the core is then determined to ascertain the permeability.

In addition, prior to the filing of this invention, a patentability search was conducted which uncovered the following patents:

| Inventor | Reg. No. | Reg. Date |
|---|---|---|
| Bowman | 966,078 | Aug. 2, 1910 |
| Dietert et al. | 2,516,188 | July 25, 1950 |
| Reichertz | 2,539,355 | Jan. 23, 1951 |
| Leas | 2,618,151 | Nov. 18, 1952 |
| Herzog et al. | 2,737,804 | Mar. 13, 1956 |
| Dotson | 2,745,057 | May 8, 1956 |
| Donaldson | 3,158,020 | Nov. 24, 1964 |
| Heuer, Jr. et al. | 3,199,341 | Aug. 10, 1965 |
| McMillen | 3,839,899 | Oct. 8, 1974 |
| Wilkins | 4,043,407 | Aug. 23, 1977 |
| Turner et al. | 4,083,228 | Apr. 11, 1978 |
| Neri | 4,227,397 | Oct. 14, 1980 |
| Wiley | 4,253,327 | Mar. 3, 1981 |
| Heitmann et al. | 4,287,754 | Sept. 8, 1981 |
| Pezzi | 4,403,501 | Sept. 13, 1983 |
| Hains | 4,430,890 | Feb. 14, 1984 |
| Holt | 4,454,095 | June 12, 1984 |

The Wiley patent sets forth a method and apparatus for measuring core permeability at overburden conditions of both pressure and temperature. Furthermore, Wiley teaches the injection of the actual fluid from the formation, as well as the injection of other fluids such as corrosion inhibitors and polymers for secondary and tertiary recovery. Each core must be manually loaded into a sleeve having end plugs inserted into the sleeve. Then the entire assembly is placed into a hydrostatic cell wherein hydraulic fluid is pressurized around the end plugs and the sleeve to simulate the overburden pressure. The fluid is then injected through one end plug, through a sintered plate, through the core, out a second sintered plate and through the opposing end plug. The differential pressure is measured so that the permeability of the core can be determined.

The Herzog et al. patent provides relative permeability measurements on core samples contained in a core holder which positions each core sample in a plastic sleeve mounted within a metal cylinder so that the ends of the core sample can be subjected to various tests. The core is not placed under an overburden stress either radially or axially. The core sample must be manually loaded into the plastic sleeve which in turn threadedly engages the metal cylinder and, which must then be mounted into the core holder.

In Leas, a manually loaded cell for measuring relative permeability is disclosed wherein a flexible elastic sleeve selectively pressurizes the sides of the core during testing so as to simulate overburden stress. Fluids are injected into the end of the core to measure the permeability of the core. To insert or remove the core, a vacuum is pulled around the elastic sleeve so that the core can be manually removed or inserted. Porous disks are placed on each end of the core to aid in the distribution of the fluid to and from the core.

The Dotson patent sets forth a core sample holder which is also mechanically or manually assembled for each core measurement for determining interstitial water content and electrical resistivity wherein pressurized fluid may be introduced in a reservoir around the core positioned in the cell.

In the McMillen patent, a testing cell for determining the length, diameter, porosity, and permeability of a core sample in a single handling operation is set forth. The testing cell receives the cylindrical core sample through one end and a quick locking/releasing plug is connected over the core sample on that end. The opposing plug slidedly engages the other end of the core sample by means of a hydraulically actuated piston. The length that the piston travels is used to determine the length of the core sample. In addition, an elastic sleeve similar to that disclosed in Leas is expanded, by means of fluid pressure, around the core sample. The amount of fluid required is mathematically related to the diameter of the core and, hence, the diameter of the core can be determined.

Heuer, Jr. et al. discloses a method and apparatus for measuring compressibility of core samples by encapsulating the core sample in a fluid-impervious sheet such as flexible plastic and then suspending the core sample in a pressure vessel and subjecting the sample to high pressure while passing fluids to and from opposing ends of the core sample through perforated disks.

The Morgan patent sets forth a method of sealing cores while determining the permeability of the core by providing a counter-pressure environment around the core with an atmosphere of non-wetting fluid. The pressure eliminates the use of sealing material such as pitch, tar, or a separate sealing medium such as plastic or rubber.

The patents to Reichertz, Dietert et al., Donaldson, and Hains all relate to variations of the above approaches or to different types of tests.

The Bowman and Wilkins patents set forth approaches for mechanically holding a number of soil or core samples for conducting tests on.

The Holt patent although not related to the field of this invention, sets forth an automatic chemical analysis device utilizing a carousel to automatically position encased glass ampoules over an injection piston for selective insertion into a smashing unit for breaking the top of the ampoule. The insertion of the ampoule into the smashing chamber results in a sealed engagement of the ampoule with the chamber. Once the ampoule is smashed, a chemical analysis is performed on the contents of the ampoule.

While also not relating to the field of this invention, the search also uncovered the patents to Pezzi, Neri, and Heitmann, et al. which all relate to carousel-type machines for testing cigarettes including the air permeability of the cigarettes.

None of the above patents set forth a method and apparatus for automatically determining the permeability and porosity of multiple core samples wherein each core sample is automatically loaded into a testing cell and wherein the two tests are conducted automatically. The McMillen patent sets forth a cell which is manually loaded and, once manually loaded, is capable of automatically performing length, diameter, permeability, and porosity tests. However, between each set of tests, the McMillen cell must be manually disassembled to remove the core sample.

The present invention provides an automatic carousel loading apparatus and method which positions each core sample of a multiple number of core samples, each of varying length but of relatively constant diameter, above a lower piston which when activated moves the core sample upwardly into the testing cell. Once inserted into the testing cell, the piston holds the core sample in a sealed chamber and, simultaneously, axial stress and radial stress, applied by two different sources, is placed on the core sample. A second piston, internal to the first piston, selectively opens and closes the lower end of the core sample holder to conduct permeability and porosity tests, respectively. Once these tests are automatically performed, the first piston is released to lower the core sample back into the carousel, the carousel turns and the piston inserts the next core sample into the testing chamber. In this fashion, all core samples in the testing chamber are sequentially tested for permeability and porosity without manual loading. This represents a savings of a substantial amount of time on the part of a skilled operator which savings were recognized in McMillen patent as being clearly beneficial. It is not uncommon for laboratories involved in this type of testing to conduct permeability and/or porosity tests on ten to thirty thousand core samples monthly.

SUMMARY OF THE INVENTION

The problems solved by the present invention and not found in the prior art approaches reside in the automatic loading of a predetermined number of core samples so that each individual core sample is lifted upwardly into a test chamber so that permeability and porosity tests can be automatically performed thereon and further resides in the provision of a portable number of carousels each containing a number of core samples.

The present invention solves these problems by providing a rotatable or pivotal carousel carrying the multiple core samples wherein the carousel is under the control of a stepping motor. The carousel is selectively rotated a predetermined number of steps so that each core sample is positively oriented over a piston and under the testing cell itself. An electronic alignment check is made to verify the position of the stepping motor before the piston is activated. Upon verification, the piston is activated under a first low pressure to raise the core sample upwardly into the test cell and once properly seated, the piston applies a preselected overburden axial stress to the core sample simultaneously with the application of the predetermined overburden radial stress to the sides of the core sample. The test cell chamber and piston accommodate different core sample heights. A second piston internal to the first piston is selectively operated to permit either a porosity or a permeability test to occur on the loaded core sample.

In the event that permeability is being tested, a gas is injected into the top of the core sample through the test cell, through the core sample and, with the second piston released, to the bottom of the core sample and out to the atmosphere. In the event that a porosity test is being performed, the second piston is activated to seal the bottom end of the core sample so that the pore volume of the core sample can be ascertained. Upon completion of the test, the piston automatically lowers the core sample from the test cell and returns it to the carousel which is then rotated or advanced to the next position. In this fashion, each core sample is successively and automatically tested for porosity and permeability. In the event that the core sample is missing or its length is too short for proper testing, the system of the present invention automatically skips that position in the carousel and advances to the next core sample. Finally, in the event that the piston raising the core sample should fail, an electronic detector detects the absence of the core or the piston in the test cell and prevents the activation of the radial stress forces.

In an alternate embodiment the carousel can be easily inserted and released from the present invention, so that a number of labelled carousels with labelled cores can be preloaded and suitably identified for testing by a number of different testing machines including the determination of porosity and permeability.

DESCRIPTION OF THE DRAWING

FIG. 3 is a partial cut-away perspective of the intensifier body;

FIG. 4 is an upper view of the intensifier body of FIG. 3;

FIG. 5 is a bottom view of the intensifier body of FIG. 3;

FIG. 8 is a perspective view of the elastic sleeve;

FIG. 9 is a top planar view of the perforated end plug plate of the present invention;

FIG. 10 is a cut-away view of the perforated end plug plate along lines 10—10;

FIG. 11 is a cut-away view of the perforated end plug plate of FIG. 9 along lines 11—11;

FIG. 14 is a partial cut-away perspective view of the electronics ring of the present invention;

FIG. 15 is a top planar view of the electronics retainer ring of FIG. 14;

FIG. 20 is a cut-away perspective view of the lower end cap of the axial stress piston;

FIG. 21 is a cut-away perspective view of the lower portion of the axial stress piston;

GENERAL DESCRIPTION

Figure 1:
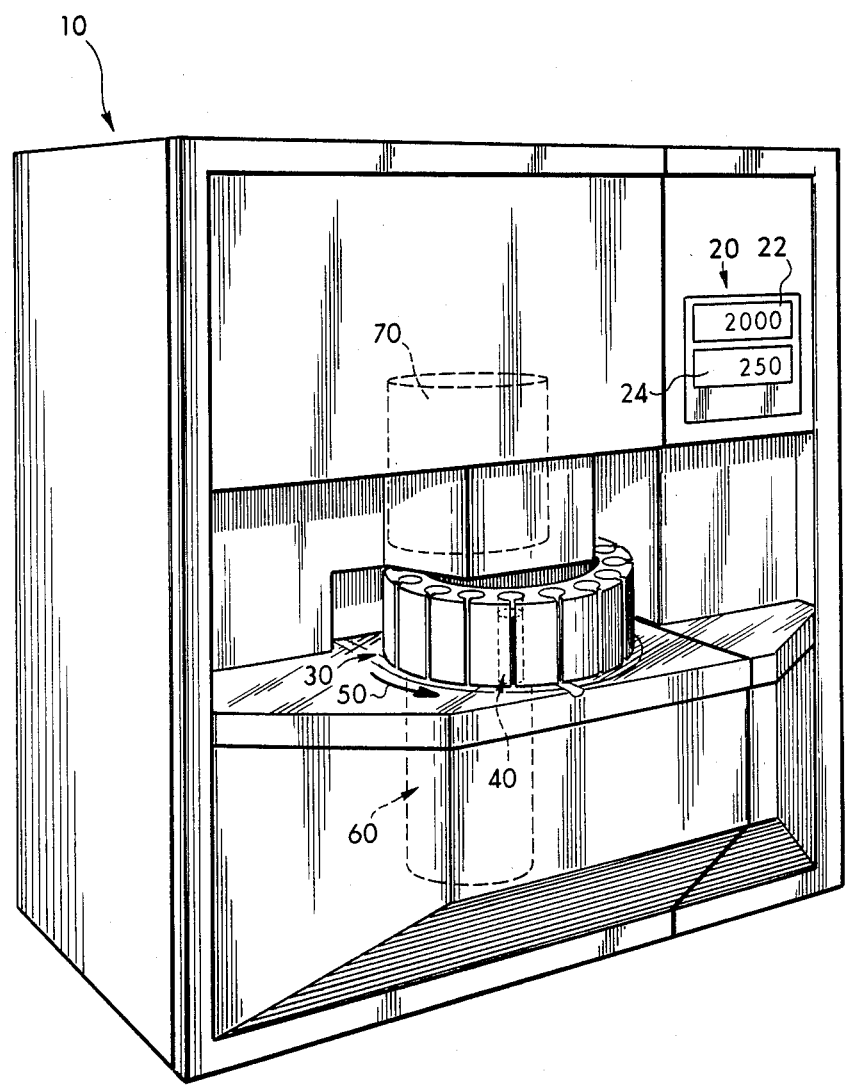
FIG. 1 is a perspective view of the porosity and permeability automatic testing machine of the present invention.

In FIG. 1 is shown the core testing carousel instrument of the present invention to include a main housing 10, a display 20 and a carousel mechanism 30. The carousel 30 holds, in the preferred embodiment, up to eighteen cores 40 of relatively constant diameter (i.e., plus or minus 0.01 inch), but of varying lengths. As will be subsequently discussed, the carousel 30 is loaded with cores 40 and the invention automatically determines the Klinkenberg permeability, the Klinkenberg slip factor, the Forchheimer turbulence factor, and the pore volume of each of the cores automatically by rotating the carousel 30 in the direction of arrow 50 until all of the cores 40 have been individually tested.

The following described invention relates to the design of carousel mechanism 30, the axial stress mechanism (or lower piston) 60, and the radial stress mechanism (or sample holder) 70. As will be subsequently explained, the axial stress mechanism 60 contains a cylinder and piston for lifting each individual core sample 40 from the carousel 30 upwardly into the sample holder 70 with a low pressure force. The axial stress mechanism 60 and the sample holder 70 then cooperate together to simultaneously form a test cell or chamber for the held core sample and functions to simultaneously apply both axial and radial forces to the core, at stresses simulating the overburden forces that the core would experience in its natural environment. The overburden stress, for the example shown in FIG. 1 in display 22, is 2000 psi. The second display 24 indicates the pressure of the gas (such as helium) being applied to the core for testing.

The details of the sample holder 70, the axial stress mechanism 60, and the carousel 30 mechanism will be discussed in the following sections. A discussion of the operation of the invention follows. And finally, alternate embodiments for the internal piston and carousel are presented.

DETAILED DESCRIPTION

1. Radial Stress Mechanism (Sample Holder) 70

Figure 2:
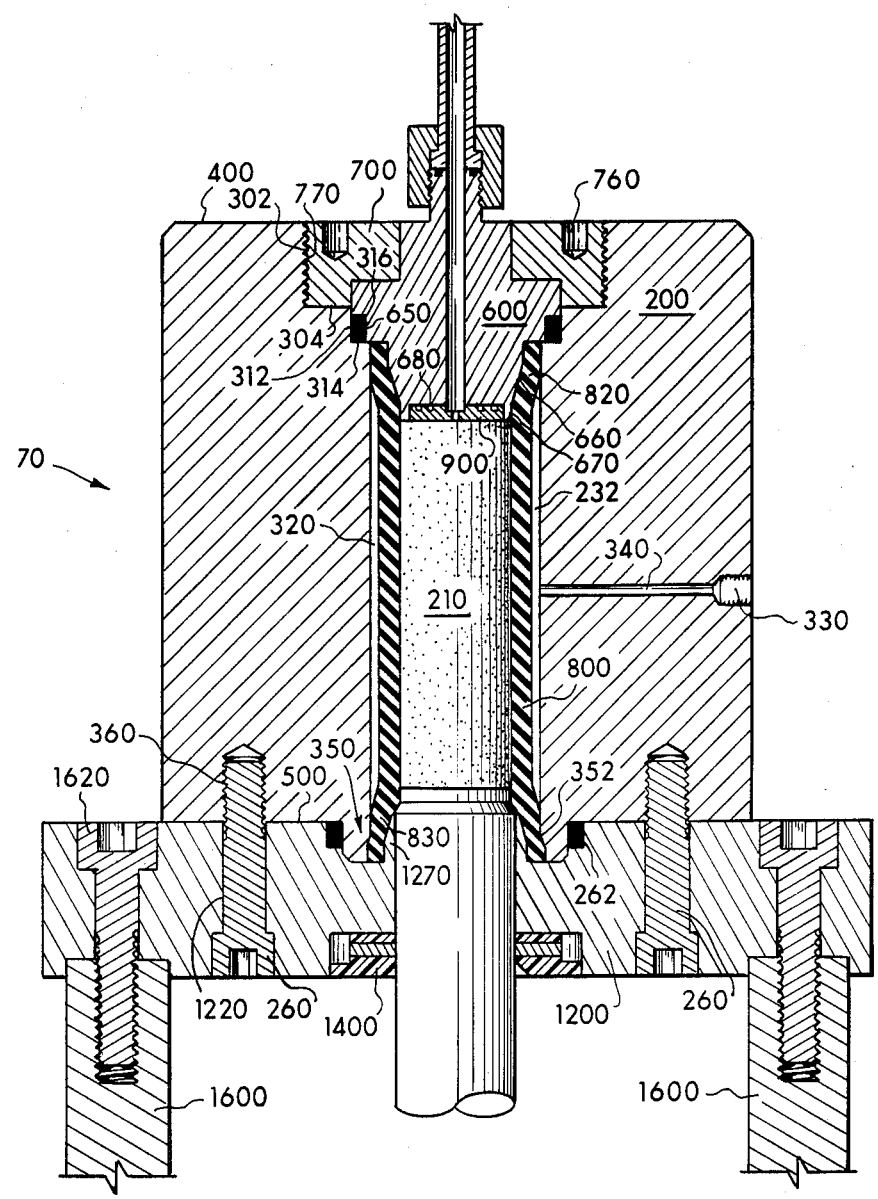
FIG. 2 is a cross-sectional view of the radial stress mechanism of the present invention.

FIG. 2 sets forth the details of the sample holder 70 to include a main cylindrically shaped body 200, an upper end plug 600, an upper retainer plug 700, a rubber sleeve 800, and an upper perforated end plug plate 900. The sample holder 70 functions to apply high radial stress to a loaded core sample 210 and in cooperation with the lower piston 60 to perform the permeability and the porosity tests.

The construction of the body 200 is set forth in FIGS. 3, 4, and 5. In the preferred embodiment, the body 200 is machined or cast from 7075-T6 aluminum alloy. The body 200 is cylindrically shaped having an upper flat end 400, as shown in FIG. 4, and a lower flat end 500, as shown in FIG. 5. Disposed on the upper end 400 is a first formed hole 300 having sides 302 and a bottom edge 304. The hole 300 is centrally located in cylinder 200 about a center axis 306. The side 302 is threaded as shown in FIG. 3. A formed hole 300 terminates in ledge 304, a second formed hole 310 of smaller diameter is formed about axis 306. The second formed hole 310 has a formed annular seat 314 with smooth sidewalls 312. Finally, a third formed hole 320 centrally located around axis 306 extends the entire longitudinal length of body 200 and forms a passageway therethrough. On one side of body 200 is a formed inlet passageway 340 having a threaded inlet 330 capable of receiving a coupling from a high pressure oil source, not shown. The high pressure oil is delivered through the formed passageway 340 from the coupler 330 inwardly to hole 320.

On the bottom flat surface 500 of body 200, as shown in FIGS. 3 and 5, is a formed annular lip 350. The inner diameter of lip 350 is slightly larger than the inner diameter of passageway 320 and a slant edge 352 interconnects the inner wall of passageway 320 with the inner wall of lip 350. This slanted inner wall is termed 352 in FIG. 5. Also disposed on the bottom end 500 are a plurality of bolt holes 360 disposed at 45 degree spacings approximately midway between the inner passageway 350 and the outer cylindrical surface of body 200.

Figure 6:
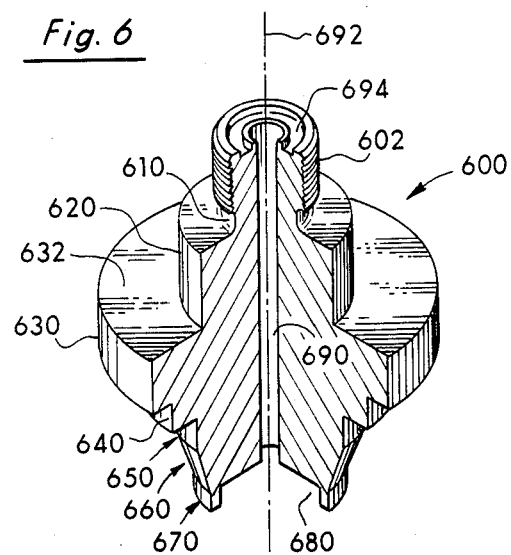
FIG. 6 is a partial cut-away perspective view of the upper end plug of the present invention.

The details of the upper end plug 600 are shown in FIG. 6. This piece is preferably machined from No. 17-4PH hardened stainless steel stock and includes an upper threaded coupler 602 interconnected through an inwardly curved directed channel 610 to a first cylindrical portion 620. The first cylindrical portion 620 terminates in a second cylindrical portion 630 of increased diameter which in turn terminates in a third cylindrical portion 640 of lesser diameter. Finally, the upper end plug 600 terminates in a cone-shaped portion 650 tapering inwardly along region 660 to a fourth cylindrical portion 670. Formed in the fourth cylindrical portion 670 is an annular seat 680. A formed passageway 690 extends the longitudinal length of the upper end plug 600 and is centered around axis 692. Formed in the upper end of the coupler 600 is an O-ring groove 694.

With reference back to FIGS. 3-5, the upper end plug 600 seats within the first formed hole 300 and the second formed seat 310 of body 200. A BAL seal 316 (shown in FIG. 2) is seated between the third cylindrical portion 640 of plug 600 and the inner wall 312 of the formed annular region 310. The BAL seal 316 provides both a static and dynamic fluid seal to prevent oil from flowing between body 200 and end plug 600. The BAL seal is manufactured by BAL-SEAL Engineering Co., 17592 Sherbrook Drive, Tustin, Calif. 92680.

Figure 7:
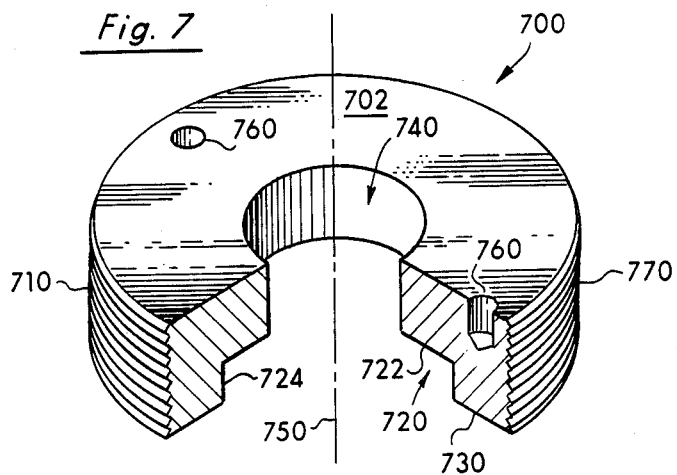
FIG. 7 is a partial perspective view of the retainer cap used in the intensifier mechanism.

The details of the retainer cap 700 are shown in FIG. 7 to include an upper flat surface 702 formed on a cylindrical body 710. A first annular region 720 is formed on the bottom surface 730 of the retainer cap 700 and communicates with a formed passageway 740. The annular region 720 and the formed passageway 740 are centrally formed in the retainer cap 700 around center line 750. The annular region 720 includes a flat seating area 722 and smooth inner sidewalls 724. Wrench holes 760 are further provided on the upper surface 702 of retainer cap 700.

As shown in FIG. 2, the retainer cap 700 holds the upper end plug 700 firmly in body 200 through the threaded engagement of threads 770 on the side of the retainer cap 700 with the corresponding mating threads 302 to body member 200. Hence, retainer cap 700 by means of wrench engaging holes 760 is turned until the upper end plug 700 firmly seats within the body 200 as shown in FIG. 2.

The details of the elastic rubber sleeve 800 are set forth in FIG. 8. The rubber sleeve 800 is cylindrical in shape having an inner passageway 810 and is made from an elastomer such as BUNA-N or VITON-A. As can be shown by reference back to FIG. 2, the upper end 820 of the rubber sleeve 800 is deformed to stretch outwardly over the lower end of the upper end plug 600 to engage firmly the cylindrical region 650, the tapering region 660, and the bottom cylindrical region 670. As can be observed, in FIG. 2, the upper end 820 of the rubber sleeve 800 is further compressed, about twenty percent, between the outer surface of cylinder portion 650 and the inner wall of passageway 320 of the body member 200. As will be explained, the stretching and compression occurring in this region provides both a static and dynamic fluid seal.

The details of the perforated end plug plate 900 are shown in FIGS. 9-11. The perforated end plug plate 900 is a cylindrically shaped washer having a plurality of formed circular arrangement of holes 905, 910, and 920 formed therethrough. The first circular arrangement of holes 905 is oriented to correspond with a first circular channel 930 and the second circular row of formed holes 910 is disposed in a second formed circular channel 940. A plurality of outwardly directed radial channels 950 is directed from an inner formed passageway 960. The third circular row of formed holes 920 is disposed only in the outwardly directed radial channels 950.

Hence, as shown in FIGS. 9 and 10, the downward surface 970, which as will be explained, abuts the upper end of the core sample, only has the exposed circular arrangement of formed holes 905, 910, 920 showing whereas the upper end 980 exposes the circular (930 and 940) and radial (950) array of channels interconnected with center passageway 960 with the formed holes 905, 910, 920 disposed therein. The perforated end plug plate 900, in the preferred embodiment, is made from 17-4PH stainless steel and press fittingly engages cavity 680 of the upper end plug 600 as shown in FIG. 2. An identical perforated end plug plate 900 is press-fitted into the upper end of the lower piston 60 so that formed holes 905, 910, and 920 contact the lower end of the core sample.

This specific arrangement of holes and channels aids in the uniform distribution of gas into and out from the core sample and provides mechanical support at the high stresses so that the ends of the core samples are not damaged. If the ends of the core sample are damaged, an error in the permeability and porosity readings could result.

Figure 12:
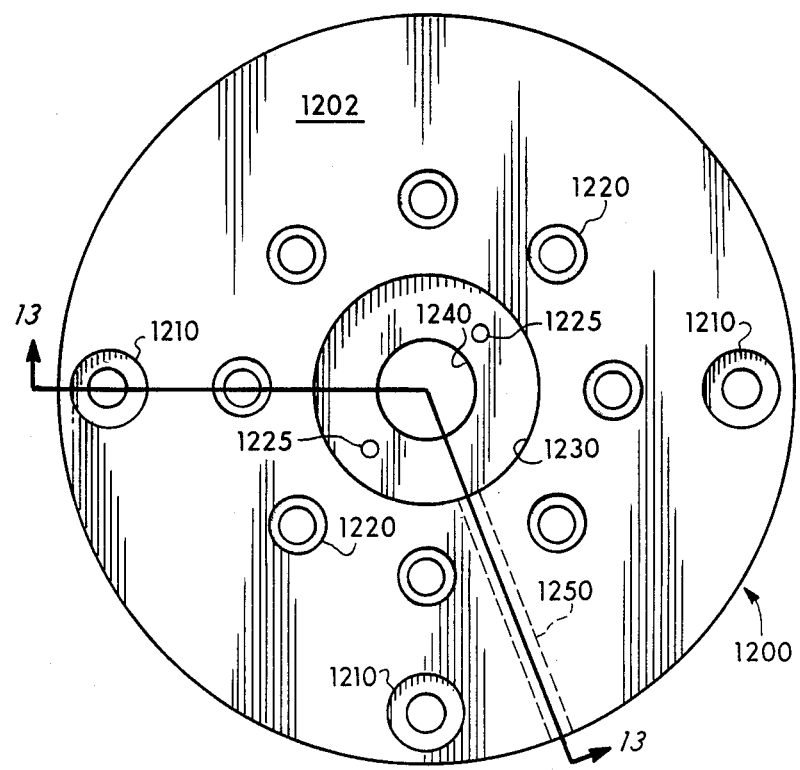
FIG. 12 is a lower planar view of the upper support plate of the present invention.
Figure 13:
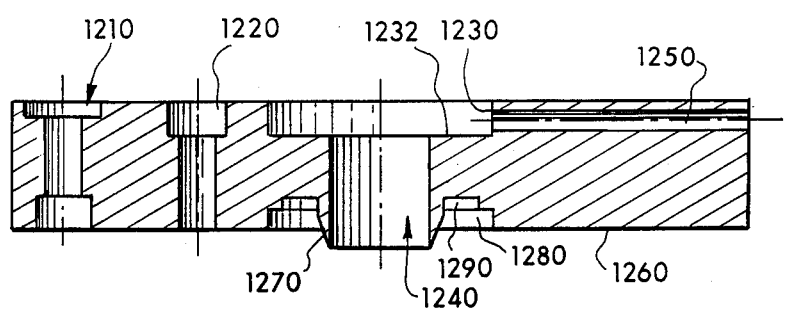
FIG. 13 is a cut-away view of the upper support plate along lines 13—13.

In FIGS. 12 and 13 are shown the details of the upper support plate 1200. The upper support plate, as shown in FIG. 12, is a circular body 1202 having three formed countersunk bolt holes 1210 formed at ninety degree spacings along a circular radius near the edge of body 1202. A second series of formed holes 1220 also designed to receive countersunk bolts is formed along a second inner radius of body 1202. In the preferred embodiment, holes 1220 are formed at spacings of 45 degrees. Finally, located in the center of body 1202 is an annular formed circular seat 1230 located around a formed circular and centrally located opening 1240. As will be subsequently explained, holes 1210 are utilized to connect to reach rods 1600 shown in FIG. 16 which connect the sample holder 70 to the lower assembly 60. Holes 1220 are utilized, as shown in FIG. 2, to connect the body 200 of FIG. 3 to the upper support plate 1200. Holes 1225 formed in annular seat 1230 retain an electronics plate 1400. Finally, in FIGS. 12 and 13 is shown a formed passageway 1250 which connects the annular region 1230 with the exterior of the plate 1200 and which functions to provide passage for electrical wires to the electronics plate 1400. The support plate 1200 is made from number 17-4PH alloy steel.

On the top surface 1260 of upper support plate 1200 is formed an upwardly extending circular dull knife edge 1270. Around the knife edge 1270 is a first circular annular region 1280 and a lower second circular region 1290 of smaller diameter. As shown in FIG. 2, the knife edge 1270 compresses the lower end 830 of sleeve 800 (approximately twenty percent) against the inner surface of lip 350 while causing the lower end 830 to be stretch deformed in regions 1280 and 1290. The compression and deformation of the end 830 effectuate both a static and dynamic fluid seal to occur as will be subsequently explained between sleeve 800 and upper support plate 1200. This knife-edge 1270 design allows the lower piston 60 to access the sample holder 70 by raising the core 210 into passageway 810 of the sleeve 800. As shown in FIG. 2, bolts 260 firmly hold the body 200 to the plate 1200 through holes 1220 and 360. A BAL seal 262 located in region 1280 provides a seal between body 200 and plate 1200.

In FIGS. 14 and 15 are shown the details of the electronics retainer ring 1400 which functions to hold a first light emitting diode 1405, a second light emitting diode 1410, and a photocell 1420. The retainer ring 260 includes a first shallow lip 1430 disposed around a raised circular ridge portion 1440. Opposing holes 1442 are formed in the sides of circular ridge 1440 to receive LED 1405 and photocell 1420 which are contained therein by a light press-fit. The outer shallow lip 1430 is integral with a raised lip portion 1450 which is not quite as tall in height as the circular ridge 1440. In the center of this raised lip portion 1450 is a formed hole 1452 which is receptive of LED 1410.

The retainer ring 1400 of the present invention is designed to engage the annular region 1230, shown in FIGS. 12 and 13 of the upper support plate 1200. In this fashion, the upper surface 1444 of circular ridge 1440 abuts against the surface 1232 of the annular region 1230. A pair of screws, not shown, engage holes 1446 to firmly hold the retainer ring 260 to holes 1225 in the annular region 1230. When installed, a channel is formed between support plate 1200 and retainer ring 1400 primarily between lip 1430 and surface 1232. This channel provides sufficient space to hold the leads of LEDs 1405 and 1410 and photocell 1430 and to direct those leads through formed passageway 1250.

The formed passageway 1460 corresponds in diameter to the formed passageway 1240 of FIG. 13. A taper 1470 is provided around the opening to passage 1460 in order to guide the entry of the core sample into region 1460. The purpose of LED 1400 and photocell 1420 is to detect whether or not a core sample has entered chamber 1460 and will be discussed later. The purpose of LED 1410 is to provide a positioning signal to the carousel mechanism 30.

Figure 16:
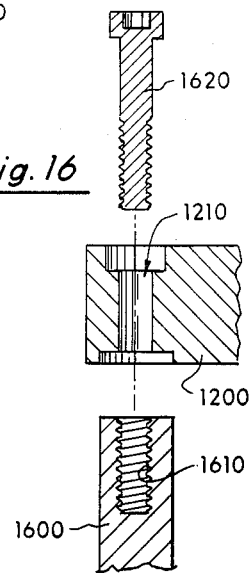
FIG. 16 is a cut-away view showing the engagement of the reach rod with the upper support plate.

In FIG. 16 is set forth the details of the reach rod 1600 which holds the radial stress mechanism 70 a predetermined distance from the axial stress mechanism 60. Each reach rod 1600 has opposing threaded holes 1610 receptive of a bolt 1620. The formed passageway 1210 is machined into the upper support plate 1200 to receive the upper end of the bolt 1620. The opposing end of the reach rod 1600 likewise engages a lower support plate and a lower bolt, not shown. In the preferred embodiment, three reach rods 1600 are utilized to separate mechanisms 60 and 70 by a predetermined distance. This predetermined distance is sufficient to allow for the selective engagement of the carousel mechanism 30.

As will be discussed later, the radial stress mechanism or sample holder 70 functions to apply a radial stress to each of the core samples approximating that of the overburden stress. In addition, the permeability and porosity tests are performed while the overburden stress is applied. While a preferred design for the radial stress mechanism 70 has been shown it is to be expressly understood that variations could be made thereto under the teachings of the present invention.

2. Axial Stress Mechanism

Figure 17:
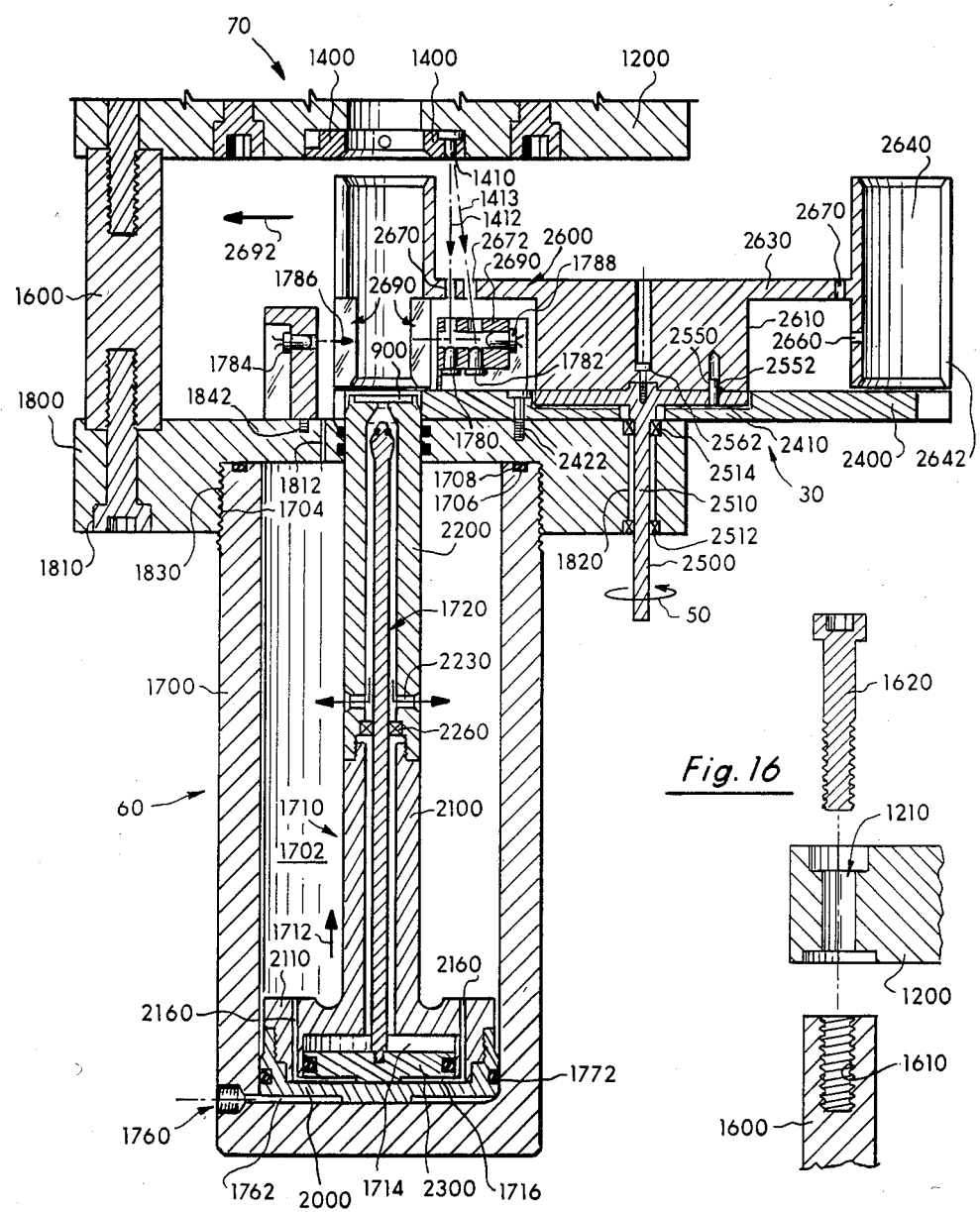
FIG. 17 is a section view of the axial stress mechanism and the carousel of the present invention.

The details of the axial stress mechanism 60 and the carousel 30 mechanism are shown in FIG. 17. The mechanism 60 includes a piston housing 1700 connected to a lower support plate 1800. Internal to the housing 1700 is positioned a first piston 1710 and a second piston 1720 is located internal thereof. The purpose of the first piston mechanism 1710 is to selectively raise a core sample from the carousel mechanism 30 upwardly into the sample holder 70. Once the core is loaded into the holder 70, the piston 1710 and the sample holder 70 provide the axial and radial stress, respectively, to the core sample simultaneously. The engagement of the first piston 1710 with the holder 70 creates a test cell or chamber for the raised core sample. The internal piston 1720 then functions to permit the performance of the two separate tests of permeability and porosity on the core sample. In particular, when the internal piston 1720 is activated (i.e., in the up position) a porosity test can be performed and with the piston 1720 deactivated a permeability test can be performed. This will be discussed subsequently.

Figure 18:
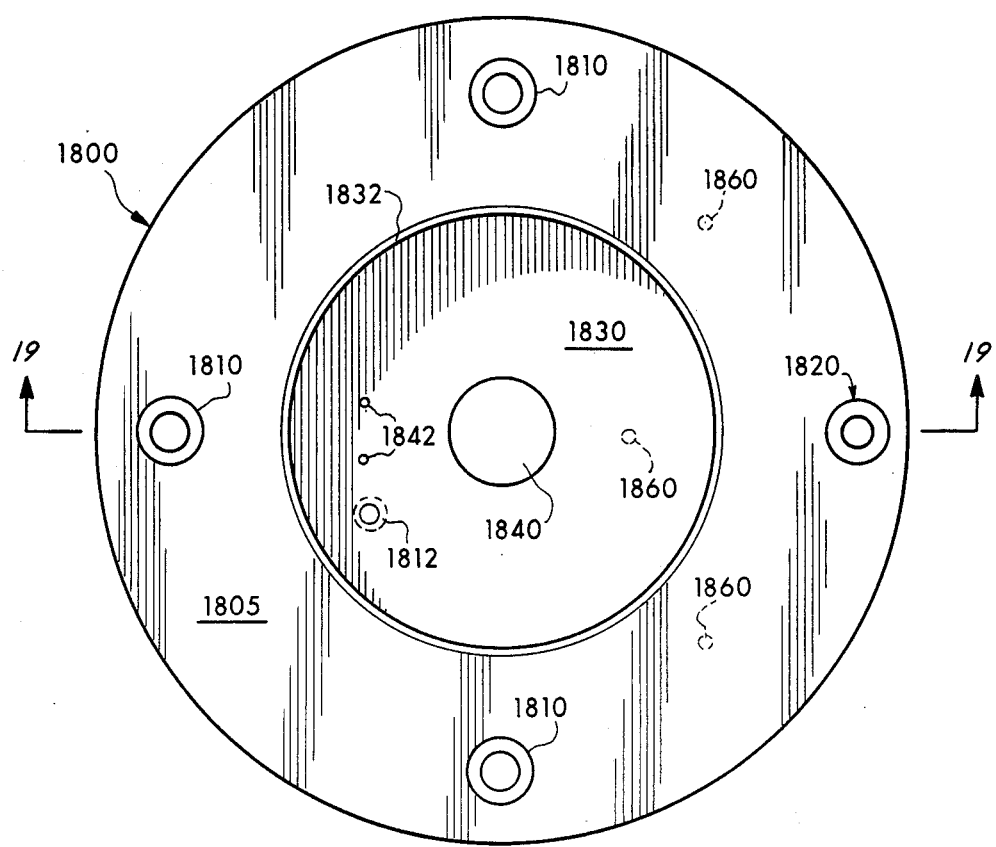
FIG. 18 is a bottom planar view of the lower support plate of the present invention.
Figure 19:
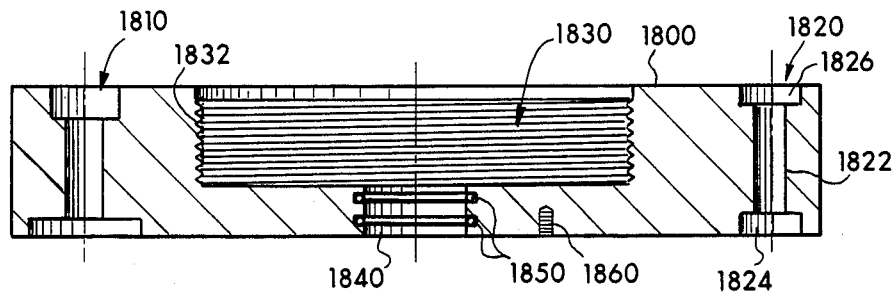
FIG. 19 is a cut-away section of the lower support plate of FIG. 18 taken along lines 19—19.

The details of the lower support plate 1800 are shown in FIGS. 18 and 19 to include a main circular body 1805 which is preferably made from aluminum alloy 7075-T6. The main body portion 1805 has three formed and countersunk bolt holes 1810 which are receptive of the reach rods 1600 as shown in FIG. 16. The countersunk holes 1810 correspond to countersunk holes 1210 of FIG. 16. The three holes 1810 are formed along a radius slightly inward from the outward radius of circular piece 1805. A fourth formed hole 1820 has a formed passageway 1822 through body 1805 with annular regions 1824 and 1826 formed on opposite faces of body 1805 and having a larger radius than that of passageway 1822. As will be explained subsequently, this formed hole 1820 is designed to engage with the carousel mechanism 30. In the center of lower support plate 1800 and on its bottom surface is a formed cavity 1830 having threaded sides 1832. Finally, a passageway or circular hole 1840 is formed at the center and has formed therein two spaced O-ring grooves 1850. As shown, in FIG. 17, formed holes 1842 in cavity are used to hold the electronics housing 1844 in place.

Formed hole 1812 is the passageway for gas to enter or exit cavity 1702, as shown in illustration in FIG. 17 (i.e., the hole 1812 is not located at the sectional cut shown, but is illustrated). Gas exits in cavity 1702 when piston 1710 is being driven upward. When gas enters passageway 1812, piston 1710 is driven downward provided port 1760 is vented. However, whether or not port 1760 is vented, the internal piston 1720 is activated when cavity 1702 is pressurized to a low pressure (i.e., 10–15 psig) with gas delivered through passageway 1812.

Finally, holes 1860 are provided so that the scuff plate 2400 can be mounted to the upper surface of the lower support plate 1800.

The axial intensifier housing 1700 shown in FIG. 17 is a cylinder formed from aluminum alloy 7075-T6 and has a cylindrical cavity 1702 formed therein. The upper outer end 1704 of housing 1700 is threaded and engages the formed cavity 1830 of the lower support plate 1800, as shown in FIG. 19. An O-ring groove 1706 and an O-ring 1708 are provided on the upper end of the housing in order to provide a fluid tight seal between housing 1700 and the lower support plate 1800. A gas fitting 1760 is further provided in order to input nitrogen gas into the region 1762 below the first piston mechanism 1710 in order to lift the piston 1710 in the direction of arrow 1712. The inlet fitting 1760 inputs the gas to the circularly formed region 1762 located between the piston mechanism 1710 and the housing 1700 as shown in FIG. 17.

In FIG. 20 are shown the details of the end cap 2000. The end cap 2000 is machined from 7075-T6 aluminum alloy and is substantially cylindrical in shape. On the cylindrical sides of end cap 2000 is formed a circular groove 2005 which, as shown in FIG. 17, is receptive of O-ring 1772. The O-ring provides a static and dynamic fluid seal between the end cap member 2000 and the interior cylindrical surface of the housing 1700. The cylindrical portion 2010 around the formed groove 2005 is of greater diameter than the upper remaining portion of the cylindrical structure 2020. The bottom end 2030 of the end cap 2000 includes a centrally located raised circular portion 2032 terminating in a slightly recessed circular portion 2034. The portion 2034 being slightly recessed cooperates with the lower surface of housing 1700 to form a region 1762 as shown in FIG. 17. Wrench holes 2036 are provided for a spanner wrench in order to screw the end cap 2000 onto the remaining portion of the piston mechanism 1710. Formed in the upper end of the end cap 2000 is a first circular chamber 2040 opening outwardly into a second chamber 2050 of greater diameter. The sidewalls 2052 of chamber 2050 are threaded.

The details of the axial piston member 2100 of the piston mechanism 1710 are shown in FIG. 21. The piston 2100 has an enlarged cylindrical head region 2110 having a first outer cylindrical portion 2112 being the same diameter as region 2020 of end cap 2000. Disposed directly beneath the enlarged cylindrical head portion 2112 is a threaded cylindrical portion 2114 which engages the threads 2052 of the end cap 2000 as shown in FIG. 20. The threaded region 2114 is of reduced diameter than the outer head portion 2112. The threaded region 2114 terminates in yet a third cylindrical portion of decreased diameter 2116. At the bottom of the axial piston member 2100 is a formed cavity 2120 which as shown in FIG. 17 cooperates with formed cavity 2040 to form a chamber 1714 as shown in FIG. 17. Centrally disposed through the center of piston member 2100 is a formed passageway 2130. Passageway 2130 terminates in cavity 2120 after undergoing a chamfered end 2132. The upper end of cylinder head portion 2112 is integrally connected to a cylindrical shaft 2140. An arcuate channel 2142 is formed between head portion 2112 and shaft 2140. The upper end of shaft 2140 terminates in a threaded portion 2150 of decreased diameter.

As shown in FIG. 17, the piston 2100 member firmly engages the end cap 2000 to form an overall piston head to the piston mechanism 1710. In addition, a formed chamber 1714 is contained within this piston head for containing the head of the internal piston 1720. Finally, two formed passageways 2160 are formed at 180 degree intervals around the piston head 2110 which function to provide fluid communication into chamber 1714. As will be explained subsequently, pressurized gas delivered through this fluid passageway 2160 serves to activate or deactivate the internal piston 1720.

Figure 22:
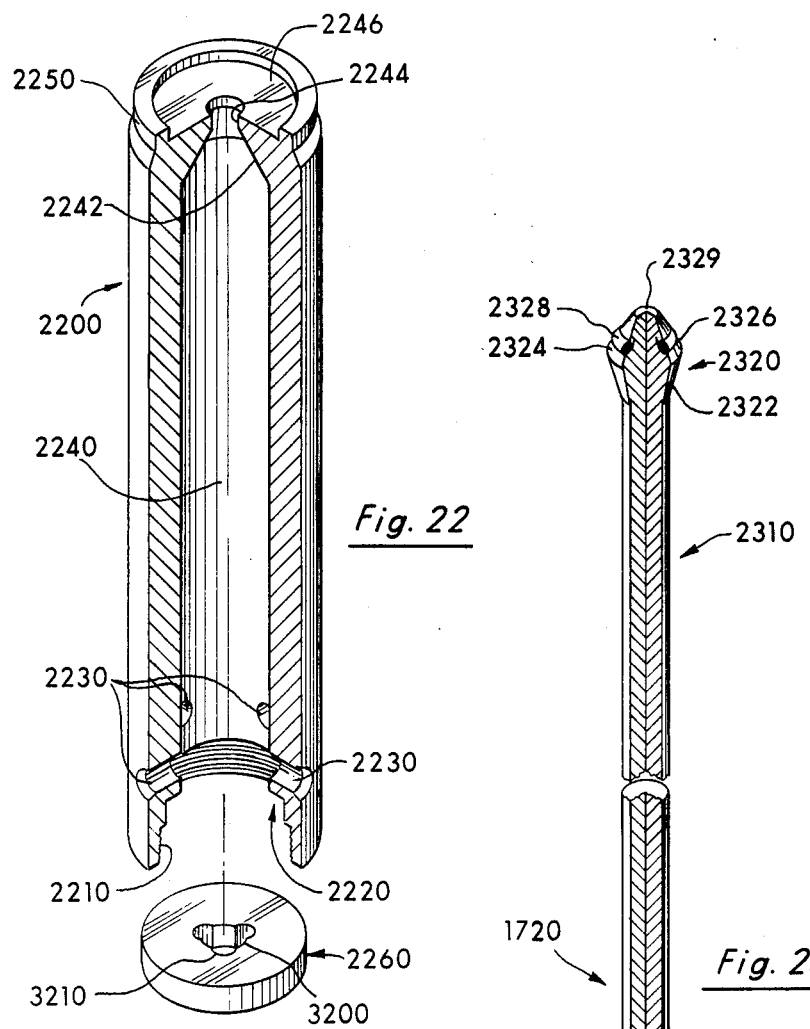
FIG. 22 is a partial perspective view of the piston extension of the present invention with an exploded perspective view of a centering ring.

The details of the piston extension 2200 are shown in FIG. 22. The piston extension 2200 forms an extension of shaft 2140 of the axial piston member 2100. The piston extension is made from alloy steel material number 17-4PH (H-900). The piston extension 2200 is cylindrical in shape. In the lower end of extension 2200 is formed a threaded annular region 2210 which engages the threaded end 2150 of the axial member 2100. Directly above the threaded annular region 2210 is a formed annular cavity 2220 of slightly smaller diameter. Directly above this cavity 2220 are four formed vent passageways 2230. The formed passageway 2240 longitudinally and centrally located in extension 2200 is a continuation of and is of the same diameter as formed passageway 2130 of member 2100. The upper end of passageway 2240 terminates in an inwardly directed cone region 2242 which then terminates in a formed circular passageway 2244 of much smaller radius than of passageway 2240. Passageway 2244 enters a formed annular region 2246 located at the extreme top of extension 2200. The top end 2250 of extension 2200 is of slightly decreased diameter being integral through a tapered region with shaft 2200.

Figure 23:
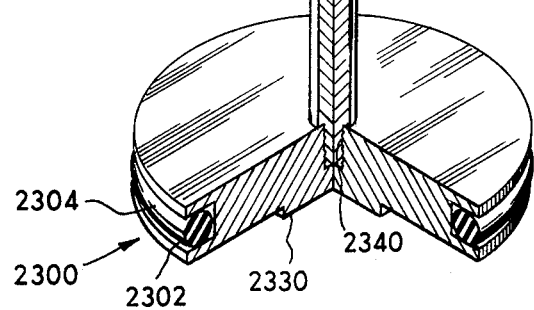
FIG. 23 is a partial cut-away perspective view of the internal piston of the present invention.

The extension 2200, as mentioned, screws onto end 2150 of the axial portion 2100 to extend the piston shaft as shown in FIG. 17. However, before being screwed on, a centralizing ring 2260 is inserted onto shaft 2310 as shown in FIG. 23. This upper shaft portion of the internal piston assembly is inserted into the central opening 2240 of part 2200 and centralizing ring 2260 is inserted into cavity 2220 and then end 2150 is screwed in. All will become clear, the centralizing ring 2260 stabilizes the inner piston mechanism 1720. A second perforated end plug plate 900, shown in FIGS. 9 through 11, is press fittingly inserted into the annular region 2246 with the circular hole arrangement side 970 up in order to abut the lower end of the core sample.

In FIG. 23 are shown the details of the internal piston mechanism 1710. The internal piston 1720 consists of two parts. A lower head 2300 and an upper shaft portion 2310 terminating in a plug 2320. The lower head portion 2300 is cylindrical in shape having a diameter equal to slightly less than the diameter of cavity 2120 of the axial piston member 2100. Formed in this region is O-ring groove 2302 holding an O-ring 2304. The O-ring 2304 provides a fluid seal between head 2300 and the inner surface of chamber 1714. At the bottom of the head 2300 is a circular portion 2330 which is slightly raised from the cylinder head portion 2300 to form cavity 1716 as shown in FIG. 17. The purpose of cavity 1716 is to provide a flow path for the gas injected through passageways 2160 in order to raise and lower head 2300. The shaft 2310 threadedly engages the head as shown in region 2340.

The material used to manufacture the head 2300 and the shaft 2310 is an aluminum alloy, number 6061-T6. At the upper end of the shaft 2310 is a formed plug 2320. The shaft 2310 terminates in an outwardly directed cone region 2322 which, in turn, terminates in an inwardly directed cone region 2324 having formed thereon a circular groove 2326 receptive of an O-ring 2328. The top of the plug 2320 terminates in a flat upper surface 2329. The purpose of the plug 2320 is to selectively engage the formed conical chamber 2242 of the extension piece 2200 of FIG. 22 in order to selectively open and close passageway 2244 contained therein. The O-ring 2328 when firmly abutting against surface 2242 provides a gas seal to prevent any passage of gases from area 2240 downwardly into passageway 2240.

The operation of the two piston mechanisms 1710 and 1720 will be discussed later for performing the functions of (1) lifting each core sample from the carousel, (2) applying an overburden axial stress to each raised core sample, and (3) selectively enabling the permeability and/or porosity tests to occur. While an embodiment of the two pistons has been shown in FIGS. 17 through 23, changes and modifications may be made thereto under the teachings of the present invention.

3. Carousel 30

In reference back to FIG. 17, the carousel 30 of the present invention performs the function of holding multiple core samples and, under control of a stepping motor, of orienting each core sample over the axial stress mechanism 60 so that the core can be raised into the radial stress mechanism or sample holder 70. The carousel mechanism 30 includes a scuff plate 2400, a pivotable flange 2500, and a carousel or carrier 2600. The scuff plate 2400 is firmly attached to the axial stress mechanism 60 and the flange 2500 and attached carrier 2600 is rotatable thereon as a single unit.

Figure 24:
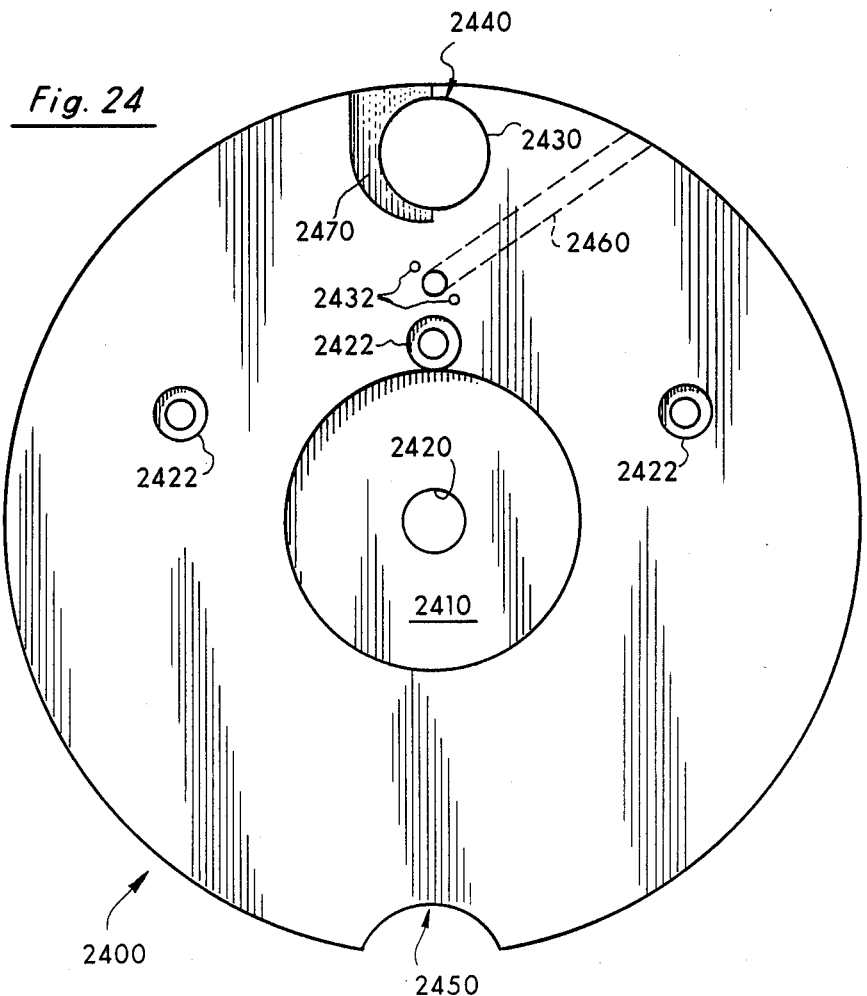
FIG. 24 is a top planar view of the scuff plate of the present invention.

In FIG. 24, the details of the scuff plate 2400 are shown. The scuff plate 2400, as shown in FIG. 17, provides the support base for the carousel 2600. The scuff plate 2400 is circular and is made from aluminum alloy material number 6061-T6. At the center of the plate 2400 is a countersunk pad 2410 and a circular passageway 2420 which extends through the plate 2400. A notch 2450 is cutoff in the scuff plate to aid in the insertion of sample cores into the carousel 2600. Disposed near the circular pad 2410 are three countersunk support holes 2422 which are receptive of bolts, not shown, to selectively engage formed threaded holes 1860 in the lower support plate 1800. The affixation of the bolts through these countersunk holes 2422 and threaded holes 1860 firmly holds the scuff plate 2400 to the lower support plate 1800 as shown in FIG. 17. Disposed on the end of scuff plate 2400 opposite cutout 2450 is yet another circular formed passageway 2430 which aligns itself with the formed passageway 1840 of the lower support plate 1800 and which provides a passagewy through which the piston mechanism 1710 can pass. Additionally, formed holes 2432 are provided for retaining an electronics package 2690 as shown in FIG. 17. A formed passageway 2460 carries the wires from the package 2690.

A beveled area 2470 is provided on the top of the scuff plate 2400 as shown in FIG. 24 in order to avoid damage to the core above the axial stress mechanism 60 upon rotation of the carousel 2600.

Figure 25:
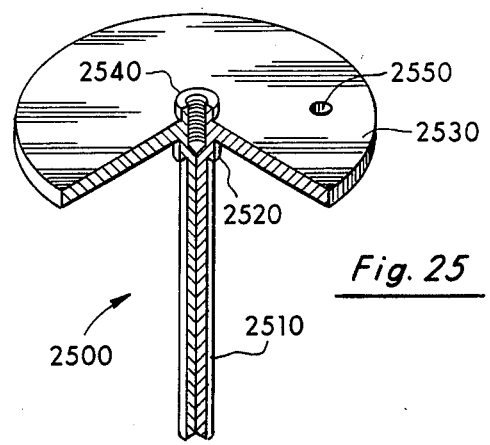
FIG. 25 is a partial cut-away perspective view of the carousel flange of the present invention.

The details of the carousel flange 2500 are shown in FIG. 25. The flange 2500 is preferably made from number 303 stainless steel material. It has a lower vertically and downwardly extending shaft 2510 terminating at the upper end in an enlarged diameter cylindrical region 2520 which is interconnected to the upper circular plate 2530. Centered on the upper surface of the plate 2530 is an upstanding cylindrical region 2540. Finally, near one end of the circular plate 2530 is a formed pin hole 2550.

As shown in FIG. 17, two bearings 2512 and 2514 hold the shaft 2510 of the flange 2500 in the formed bearing channels 1824 and 1826 as shown in FIG. 19 of the lower support plate 1800. The pin 2552 seats in the formed hole 2550. The carousel flange 2500 is capable of rotating freely on the formed circular pad 2410 of the scuff plate 2400, rotating on bearings 2512 and 2514. As will be explained, the lower end of shaft 2510 is mechanically interconnected with a stepping motor.

Figure 26:
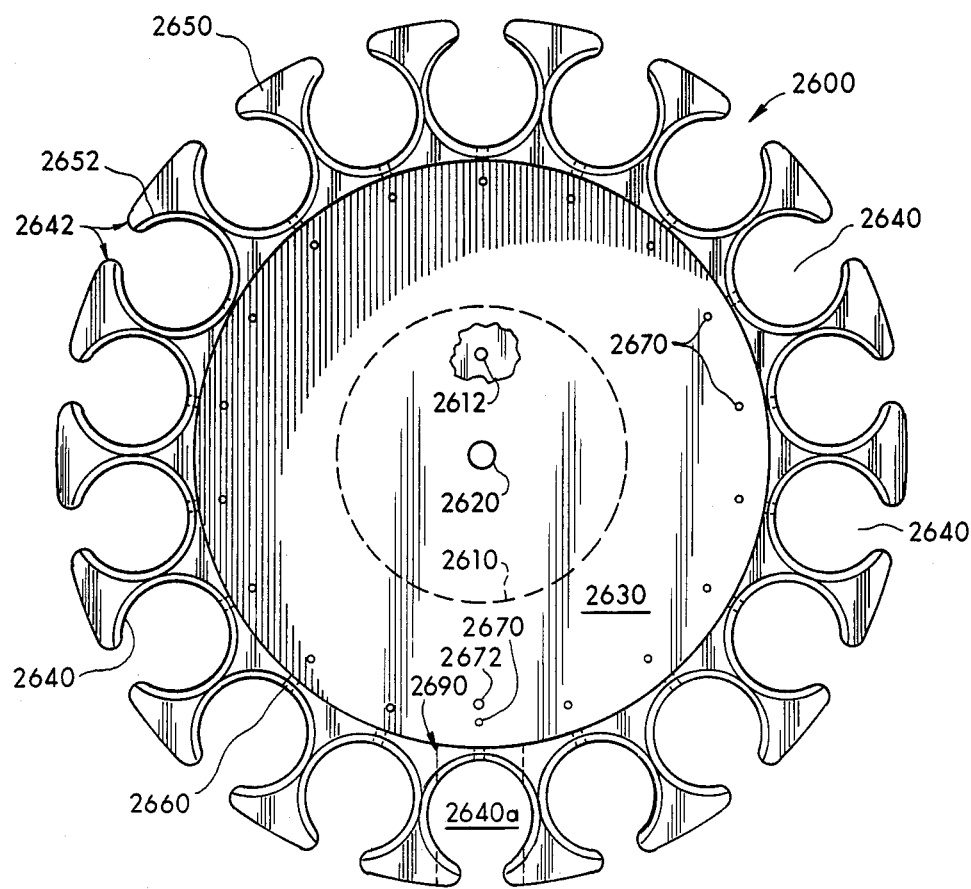
FIG. 26 is a top planar view of the carousel carrier of the present invention.

The top view of the carousel or carrier 2600 is shown in FIG. 26. Carrier 2600 is preferably manufactured from aluminum material, alloy number 6061-T6 or it can be molded from a suitable plastic material. The carrier 2600 is cylindrical in shape and includes at its bottom a centrally located cylindrical pedestal 2610. Pedestal 2610 has formed in the bottom thereof a pin hole 2612 which is receptive of pin 2552. Pin 2552 functions to lock the carrier 2600 to the flange 2500 so that both rotate as one unit. Centrally disposed in the carrier 2600 is a formed passageway 2620 which permits a screw 2562 to engage formed threaded passageways 2540 of the flange 2500. The engagement of the screw 2562 firmly attaches the carrier 2600 onto the flange 2500 and allows the flange and carrier to rotate over the scuff plate 2400.

Outwardly extending from the cylindrical portion 2610 is a circular thin-walled mid-section region 2630 terminating and integral with a plurality of formed core sample containers 2640 which in the preferred embodiment is eighteen in number. The core sample containers 2640 are formed in an annular ring 2650 and the tops of each formed core sample holder 2640 are beveled 2652 in order to allow easy access of the core samples into each container. In addition, each container 2640 has an elongated slot 2642 formed on the outer surface thereof which slot 2642 functions to permit the operator's fingers to hold the core sample and to allow easy insertion of the core sample into the carrier 2600. As shown in FIG. 17, the formed core sample holder 2640 extends all the way through the annular wall 2650 so that as the carousel 2600 pivots over the scuff plate 2400, the bottom of each core sample rides on the upper surface of the scuff plate 2400.

Each core container 2640 has a formed passageway 2660 which permits the detection, by means of a photocell and light emitting diode, of the presence of a sample in the holder 2640, as will be subsequently explained. In addition, directly in front of each core holder 2640 in the mid-region 2630 is a plurality of formed holes 2670 which also permit the passage of a beam of light from a light emitting diode through mid-region 2630 in order to detect the proper alignment of the carrier 2600 in a manner to be subsequently discussed. A second single alignment hole 2672 is also provided which is utilized to detect the initial or starting position of the carrier. Finally, in order to mount the carousel or carrier 2600 into the area between the upper mechanism 70 and the lower mechanism 60, a portion 2690 of one of the sample containers 2640a, as shown in FIG. 26 is removed in order to permit the carrier 2600 to slide over the top of electronics package 2690 as shown in FIG. 17.

In summary, the carousel mechanism 30 functions to provide a carousel carrier 2600 supported by a scuff plate 2400 and carrying a predetermined number of core samples to be selectively rotated by means of a pivotable flange 2500 interconnected with a stepping motor. While a preferred embodiment of the carousel mechanism 30 of the present invention has been disclosed modifications and changes can be made thereto, as exemplified by an alternate embodiment for the carousel to be discussed subsequently, under the teachings of the present invention.

4. Operation of the Present Invention

The operation of the present invention will now be described. The carousel mechanism 2600 can be inserted between the upper mechanism 70 and the lower mechanism 60 or into the machine of the present invention by sliding the carousel 30, as shown in FIG. 17, in the direction of arrow 2692. This permits the opening 2690 directly underneath the core container 2640a to slide over the top of the electronics package 2690 and to allow the carrier to slip over pin 2552. When properly oriented, the screw 2562 is then inserted through formed passageway 2620 so that the carrier 2600 is firmly attached to the flange 2500. A stepper motor is then conventionally interconnected to shaft 2510 of flange 2500 to rotate the carrier and flange, as a unit, in the direction of arrow 50.

The carrier or carousel 2600 is now ready to be loaded with the core samples and loading takes place by selectively activating the stepper motor to rotate each individual core container 2640 over the cut-out 2450 of FIG. 24 so that each core can be loaded into the carousel.

When the carousel 2600 is fully loaded, the machine can be activated to perform the porosity and permeability tests. The stepping motor will cause the carrier 2600 to rotate until the alignment hole 2672 is oriented over photocell 1782 as shown in FIG. 17. When photocell 1782 detects the presence of light through formed hole 2672, the system knows that the first core sample is in position and ready to be tested. It verifies that it is properly aligned with photocell 1782 by detecting the presence of a light beam 1413 from the light emitting diode 1410 in the electronics plate 1400 of FIG. 14 and as shown in FIG. 17. It is to be expressly understood that the stepping motor activates the carrier to turn a predetermined number of steps and then ascertains whether or not photocell 1782 detects light 1413 from diode 1410. It is clear that the proper positioning can be done by either counting the predetermined number of steps or by detecting the light. This double check provides a safety feature for proper alignment. It also does this for each of the eighteen core containers 2640 by means of passage of the light beam 1412 through corresponding holes 2670 to photocell 1780. In the preferred embodiment the stepping motor steps at 200 or 2000 steps per revolution.

Once the carousel is properly aligned, a light emitting diode 1784 issues a beam of light 1786 through the formed passageway 2660 of each core holder 2640 (or for the first core holder 2640a through cut-out 2690) into a photocell 1788. This performs the important function of detecting the proper height for the core sample. Under the teachings of the present invention, the core sample can vary in height from preferably ¾ inch to 3⅛ inches. However, if it is below the minimum predetermined height of ¾ inch, as dictated by the placement of passageway 2660 and the alignment of light emitting diode 1784 and photocell 1788 or if a core sample is missing, the system causes the motor to advance to the next core holder. If a core sample which is too short is allowed entry into the mechanism 70, severe damage can occur to the rubber sleeve 800 of the present invention.

Figure 27:
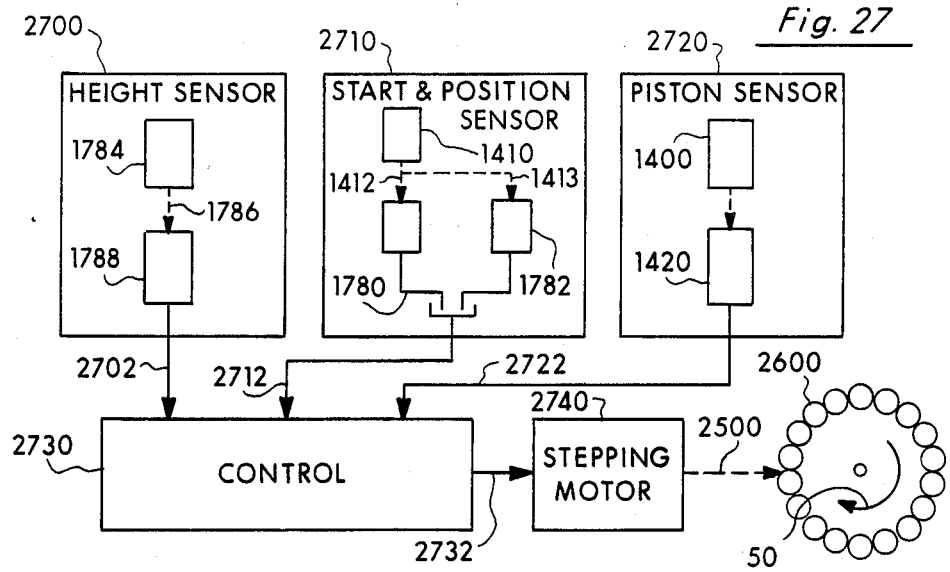
FIG. 27 is a block diagram of the electronic sensors of the present invention.

The operation of the invention to this point is best summarized by reference to FIG. 27 which shows the height sensor circuit 2700 composed of light emitting diode 1784 and photocell 1788, the start and position circuit 2710 composed of light emitting diode 1410 and photocells 1780 and 1782, and the piston sensor 2720 composed of light emitting diode 1400 and photocell 1420. These circuits respectively generate signals over leads 2702, 2712, and 2722 to a control circuit 2730. The control circuit in turn activates a stepping motor 2740 over leads 2732, the stepping motor in turn is mechanically coupled, by means of a timing belt, to the carousel flange 2500 which drives the carrier 2600 in steps in direction 50.

Figure 28:
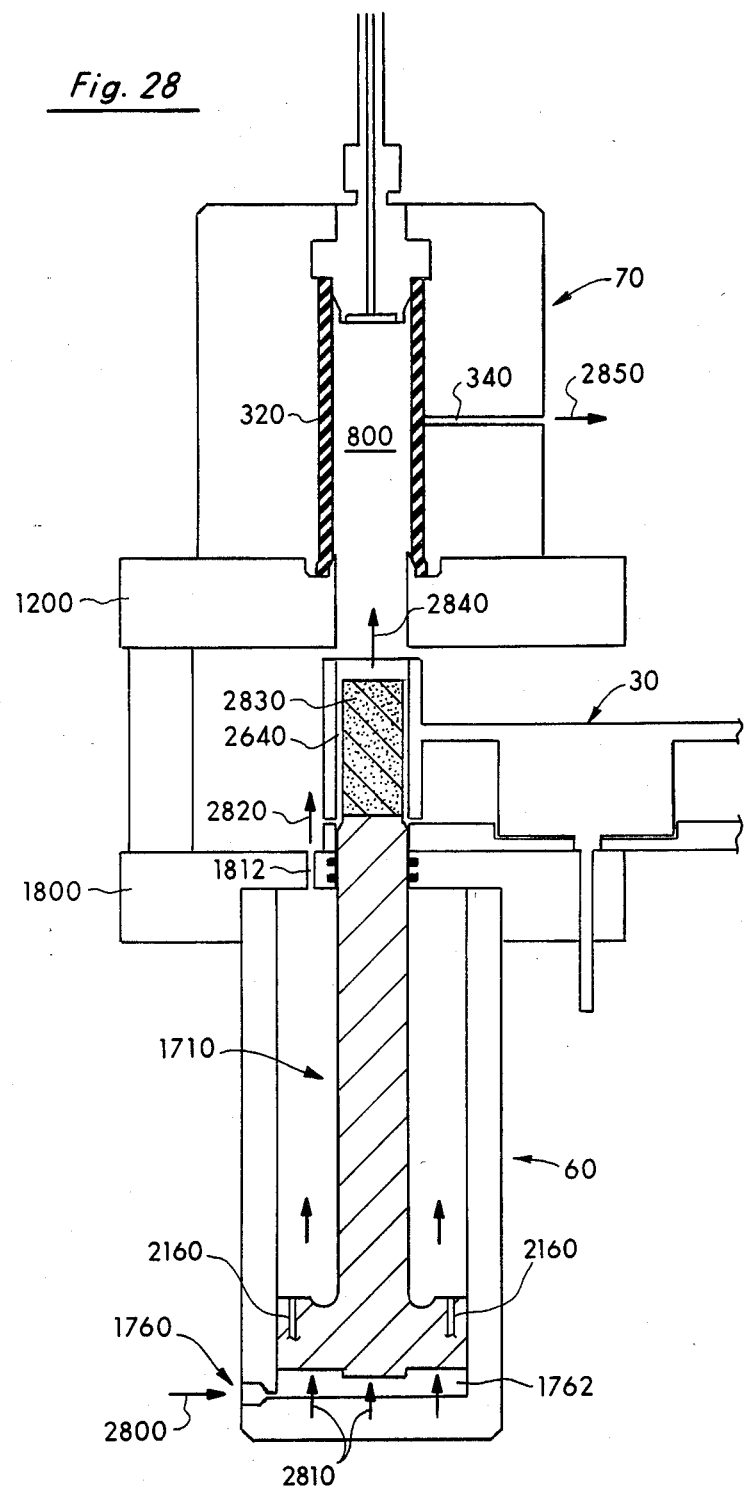
FIG. 28 is an illustration showing the operation of the axial stress piston commencing to lift a core sample.

The operation of the axial piston mechanism 1710 will now be described. In FIG. 28 is an illustration of the lifting of the piston mechanism 1710. Nitrogen gas is delivered into air inlet 1760 as shown by arrow 2800 to pneumatically activate piston 1710. This gas in cavity 1762 lifts the piston 1710 as shown by arrows 2810. The piston 1710 is driven upwardly and the gas above the piston head is vented out through passageway 1812 as indicated by arrow 2820. As the piston mechanism 1710 rises, the core sample 2830 is lifted from a positioned container 2640. The core sample 2830 is raised in the direction of 2840 into the upper mechanism or sample holder 70. During the raising of the core sample, the rubber sleeve 800 is held firmly against the inner walls of passageway 320 by means of a vacuum being drawn in the direction of arrow 2850 in passageway 340.

Figure 29:
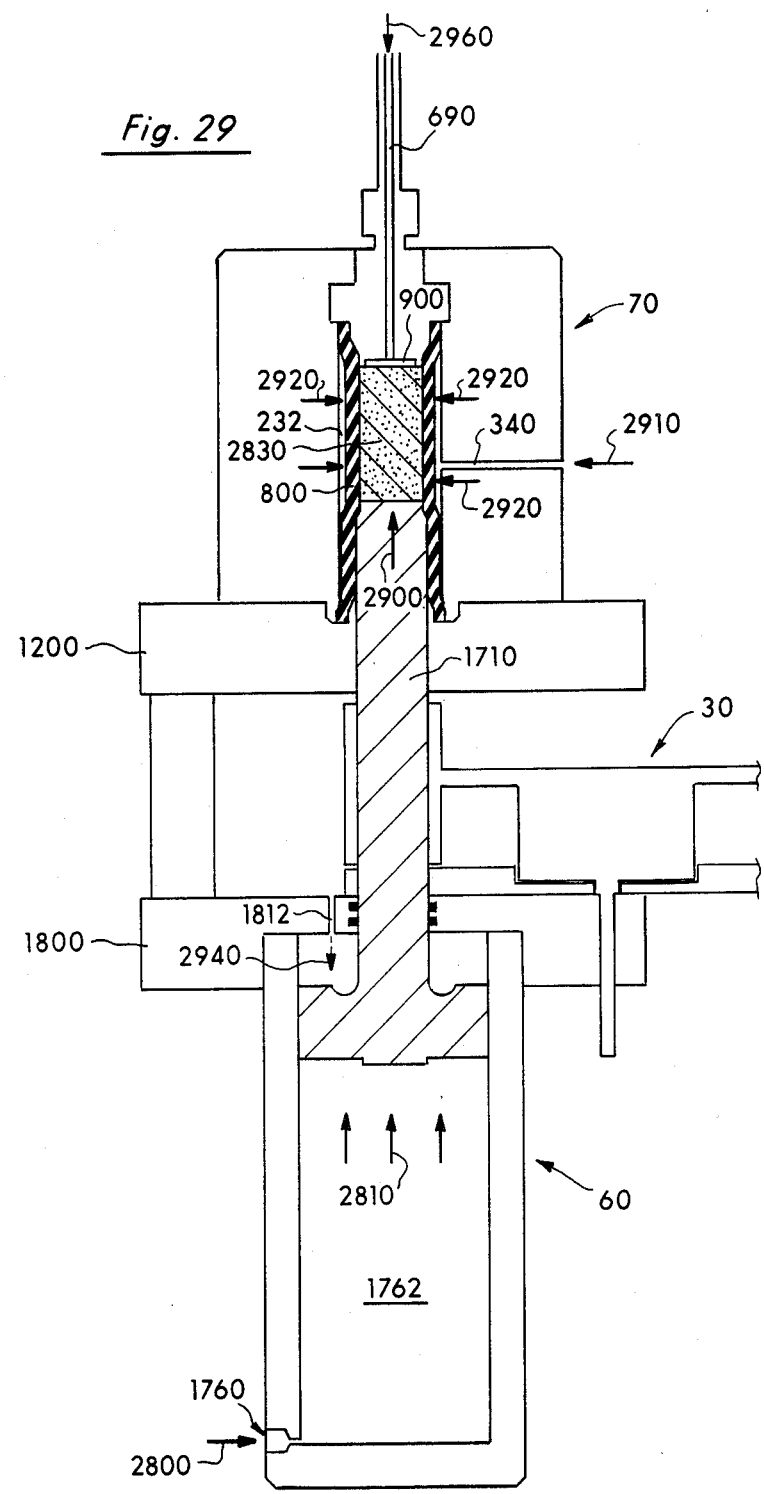
FIG. 29 is an illustration of the axial stress system holding the core sample in the sample holder with radial stress being applied.
Figure 30:
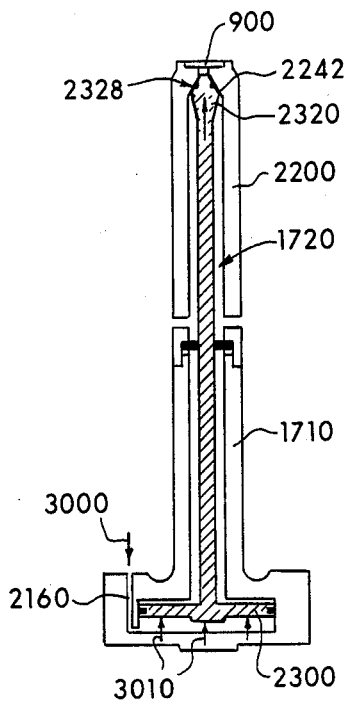
FIG. 30 is an illustration showing the internal piston closing the upper end of the axial stress piston.

In FIG. 29, the piston 1710 is fully raised and loaded into the sample holder 70. It is to be expressly understood that, under the teachings of the present invention, the piston 1710 is raised by first pressure as represented by arrows 2810 such as in the range of 10 psig to 25 psig and that once oriented in the position as shown in FIG. 29, the pressure is increased to a substantially larger value such as 50 to 1000 psig, for example, corresponding to a desired overburden stress of 500 to 10,000 psig which provides the axial stress, as shown by arrow 2900, to the core sample 2830. The axial stress 2900 being applied is typically ten times larger than the pressure represented by arrows 2810 because of the enlarged head diameter of piston 1710 in comparison to the top end of the piston. It is to be expressly understood that a single permeability test could be made at a given overburden stress or that a number of successive permeability tests, such as twenty four, could be made at successively different overburden stresses.

Simultaneously with the delivery of increased pressure to piston 1710 corresponding to the desired overburden stress, high pressure oil is delivered through passageway 340, as shown by arrow 2910, into cavity 232 causing the rubber sleeve 800 to expand around the upper end of the piston 1710 and around the core sample 2830. At this point, the core sample 2830 is subjected to both the overburden radial stress 2920 and the axial stress 2900 uniformly and continuously. As can be observed in FIG. 29, the sample core 2830 can be of any desired height within the aforementioned predetermined range of heights.

In order to release the core sample 2830, a vacuum 2850 is drawn in cavity 232 causing the sleeve 800 to return to the position of FIG. 28, and gas is added in passageway 1812, as shown by the dotted line arrow 2940, to push the piston 1710 down causing the air in cavity 1762 to vent out through vent 1760. Once fully retracted, the carousel 2600 rotates and readies the next core sample from insertion.

The operation of the inner piston mechanism 1720 which permits either the porosity or permeability tests to occur will now be discussed with reference to FIGS.

30 and 31. As the piston 1710 is moved upwardly as shown in FIG. 28, passageway 1812 is vented so that the pressure maintained above passageway 2160 is approximately 0 psig. After piston 1710 is positioned, as shown in FIG. 29, a certain amount of pressure such as 10 to 15 psig can be maintained in the area above the head of that piston.

Figure 31:
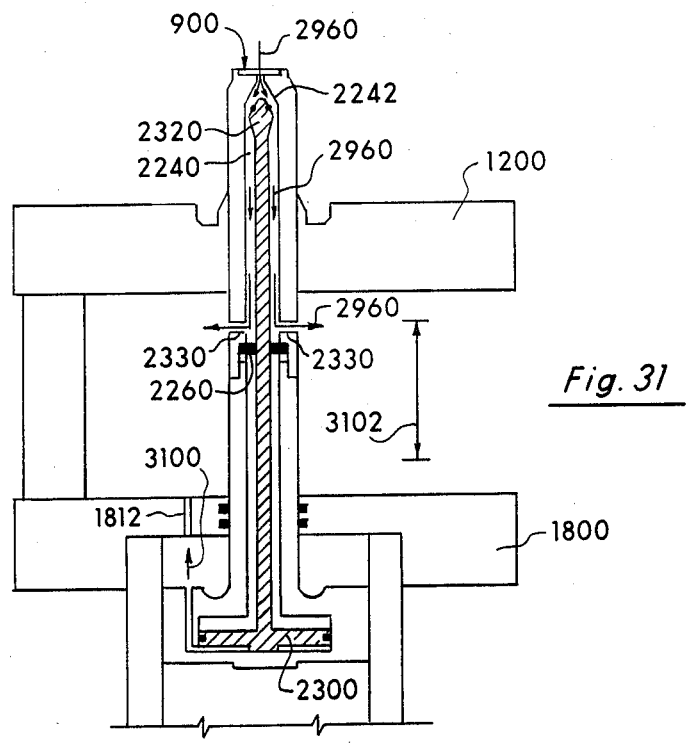
FIG. 31 is an illustration showing the internal piston opening the upper end of the axial stress piston.

This pressure represented by arrow 3000 causes a uniform uplifting pressure as shown by arrows 3010 on the head 2300 of the internal piston 1720 and causes it to lift upwardly and seat the end plug 2320 against the upper end 2242 of the piston extension 2200 with a high force. The O-ring 2328 provides a fluid seal. Hence, when the piston 1710 is in the orientation shown in FIG. 29, the maintenance of a pressure 3000 through passageway 2160 activates the internal piston 1720 to seat firmly against the upper end 2242 and to provide a fluid seal so as to prevent the passage of any gas. It is clear that at this point, the delivery of any helium gas in the direction of arrow 2960 as shown in FIG. 31 through passageway 2240 will not be permitted. Hence, a porosity or a measurement of the pore volume of core 2830 by means of a gas expansion method can take place.

When it is desired to measure the permeability of the core 2830, the pressure 3000 is removed and a vacuum is pulled in the direction of arrow 3100 through passageway 1812 as shown in FIG. 31, causing the piston head 2300 to be pushed pneumatically downwardly and causing the plug 2320 to unseat from end 2242. The helium, as shown by arrow 2960 in FIG. 29, passes through the sample core 2830 through the base plate 900 and into passageway 2240. The helium is then vented through vents 2330 to atmosphere between the upper and lower support plates 1200 and 1800. Since the core samples 2830 vary in height the venting can occur in the region designated by arrow 3102.

It is important to recognize that the permeability and porosity tests can be selectively applied without relieving the overburden stress (axial and radial) on the sample core. Further, a number of different overburden stresses can be successively applied with the tests being repeated while the core sample is held. Even the permeability and porosity tests can be conducted with different gas pressures for each overburden stress. Hence, a large number of tests can be automatically performed on each held sample.

At this point, the design of the centering ring 2260 needs to be discussed. The details of the centering ring 2260 are shown in FIG. 22. The centering ring is preferably made from a bronze bearing material and is circular in shape with a circular formed center hole 3200. However, at 120 degree spacings are placed circular cups 3210. Shaft 2310 of the internal piston 1720 fits in the formed circular hole 3200 whereas the semi-circular cups 3210 provide formed vents so that the region between the retainer ring 2260 and the head 2310 is vented to atmosphere in order to allow the internal piston to rise and fall without the creation of a vacuum in this region.

In summary, the operation of the present invention enables the first piston mechanism 1710 to travel upwardly to gently lift the sample core 2830 into the sample holder 70 and, once in position, a much larger axial stress 2900 is applied simultaneous with the radial stress 2920 to place the desired overburden stress on the core plug. In this loaded position, simulating an overburden stress, the porosity and permeability test can be performed by selectively activating (for porosity) and deactivating (for permeability) the internal piston 1720. When the internal piston is activated, the helium gas which is injected into the top of the core sample simply becomes retained in the volume of the core sample and when the piston is deactivated, the injected helium gas is allowed to travel through the core sample and is vented to atmosphere. In this fashion, the system of the present invention can automatically load and test the porosity and permeability of each of the eighteen samples. It is also to be further expressly understood that the perforated base plates 250 at the top and at the bottom of the core sample are capable of withstanding the axial and radial stresses of the present invention while minimizing damage through its unique design to opposing ends of the core sample 2830. This feature is the subject of a separate patent application filed concurrently with this application as identified above.

5. Alternate Carousel 30 Embodiment

Figure 32:
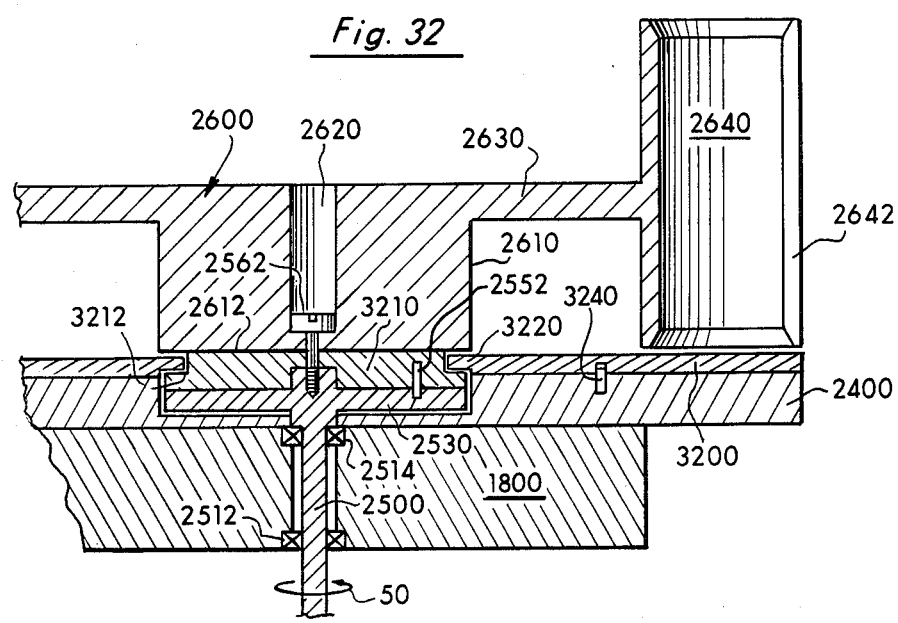
FIG. 32 is a cut-away view of an alternate embodiment of the carousel.
Figure 33:
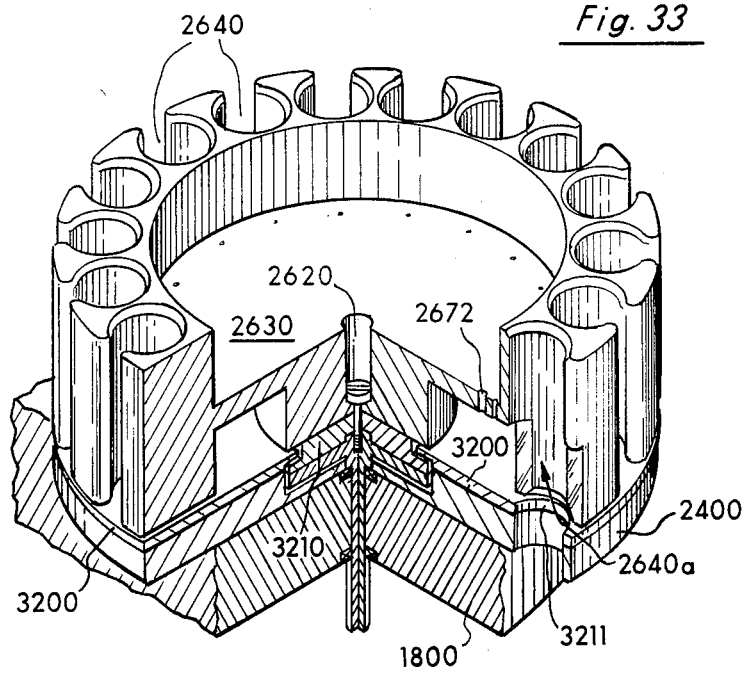
FIG. 33 is a partially cut-away perspective of the alternate carousel embodiment of FIG. 32.
Figure 34:
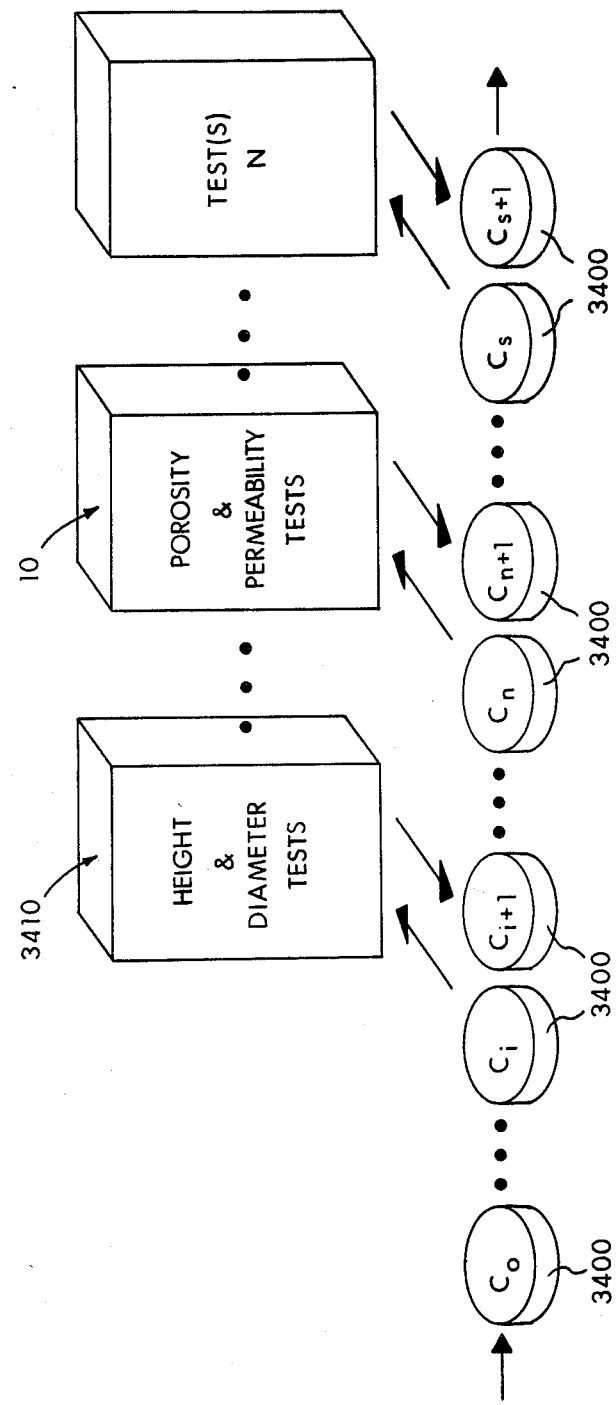
FIG. 34 is a block diagram illustration of a plurality of carousels being used to access a plurality of testing machines.

In FIGS. 32 through 34 are set forth the details of an alternate carousel mechanism 30 embodiment which primarily differs from the embodiment shown in FIG. 26 in that it is capable of being removed from between the lower assembly 60 and sample holder 70. In other words, a number of the modified carousel mechanisms 30 of the present invention can be loaded with core samples and selectively inserted into the machine of the present invention. An immediate savings is found in the continued operation of the machine whereas in the first discussed approach, at the completion of each carousel of core samples, each core sample had to be individually lifted out and a new one inserted which resulted in down-time of the machine of the present invention. With the alternate carousel embodiment, a number of carousels can be preloaded and upon the completion of a given inserted carousel, it can be removed and a new one inserted thereby minimizing the down-time of the machine of the present invention.

In FIGS. 32 and 33 the carousel of FIGS. 17 and 26 has been modified as follows. Where possible, like numbers represent corresponding parts.

In FIG. 32, two new parts are added to the embodiment of the carousel 30 shown in FIGS. 17 and 26. The first part is a carousel support plate 3200 and the second part is a pivotal transition plate 3210. The carousel support plate 3200 is positioned beneath the carrier 2600 but is not connected to the carrier 2600. Rather, the support plate 3200 is a circular plate of the same diameter as the carrier 2600 has a first inwardly extending rib 3220 which is oriented in a channel formed between the bottom 2612 of the carrier 2600 and the transition plate 3210. Plate 3210 is circular in shape corresponding in diameter to the diameter of circular plate 2530 of flange 2500. However, the upper outer end of transition plate 3210 has a formed notch 3212 which receives the inwardly extending circular rib 3220 of the support plate 3200. The transition plate 3210 is integral and firmly attached to the bottom 2610 of the carrier 2600. In this position, the transition plate 3210 firmly holds the support plate 3200 under the carrier 2600. Hence, when the modified carousel 2600, as shown in FIGS. 32 and 33, is removed from the machine, the transition plate 3210 being firmly attached to the bottom of the carrier 2600 firmly holds the support plate 3200. When the modified carousel 2600 is to be loaded into the machine, it is oriented over the previously discussed pin 2552 which engages a corresponding pin hole in the transition plate 3210 and also engages a second pin 3240 located in the scuff plate 2400 with a corresponding pin hole in the circular support plate 3200. The screw 2562 is then inserted through hole 2620 and tightens the carrier 2600 to the flange 2500 in a fashion previously discussed. Hence, the carrier 2600, the transition plate 3210, and the flange 2500 are able to freely rotate whereas the scuff plate 2400 by means of pin 3240 prevents the circular support plate 3200 from rotation.

The provision of the circular support plate 3200 and the transition plate 3210 enables carousel 30 to be easily inserted and released from the testing machine of the present invention. Because of this feature no core can reside in container 2400a (since it must slip over the electronics package 2690 and since a hole 3211 must be formed in the support plate 3200 corresponding to hole 2430 in scuff plate 2400) and, therefore, only seventeen cores can be loaded into these modified carriers 2600.

As shown in FIG. 34, a number of these carousels 3400 can be preloaded and tagged with a designation such as $C_o, \ldots C_i, C_{i+1}, \ldots C_n, C_{n+1} \ldots, C_s, C_{s+1}$. In this fashion, the preloaded carousels each containing a predetermined number of core samples can be selectively loaded into differing test machines such as, in the preferred embodiment, the porosity and permeability test equipment 10 of the present invention (shown in FIG. 1) or into other machines such as a machine for measuring the height and diameter 3410. The modified carousel of the present invention, therefore, provides a convenient testing carrier which minimizes human handling of the core samples and provides for the labeling and storage of a large number, such as thirty thousand, of core samples for quick retrieval and testing.

In addition, it is clear that the method of the present invention can be utilized for any type of test on the core which requires use of a sealed chamber with or without the application of a predetermined overburden stress.

6. Alternate Internal Piston Embodiment

Figure 35:
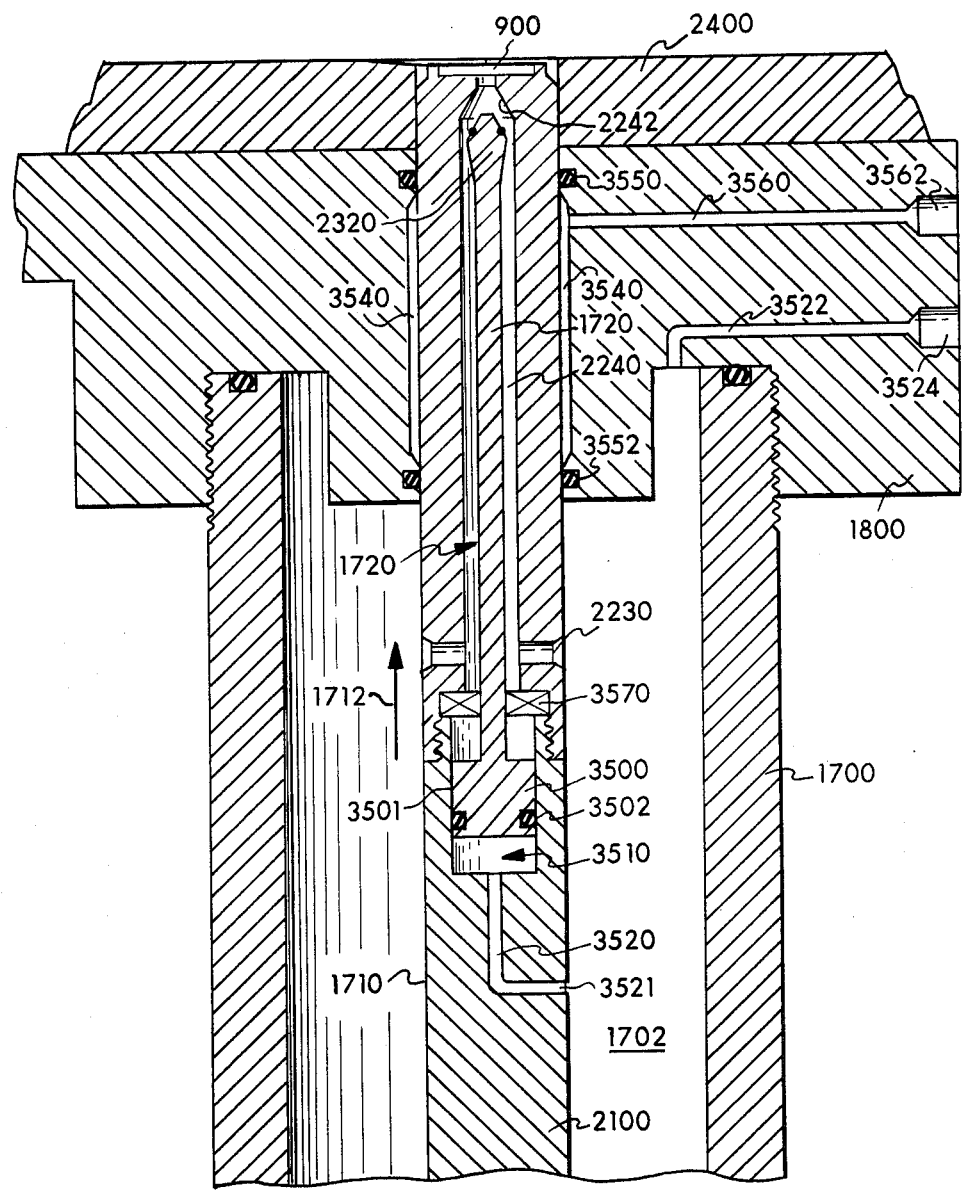
FIG. 35 is a cut-away view of an alternate embodiment of the internal piston of the present invention.

In FIGS. 17, 23, 30, and 31, are set forth the details of the first embodiment for the internal piston mechanism 1720 of the present invention. A second embodiment is shown in FIG. 35. Where possible, like components have like numerical designations.

Figure 36:
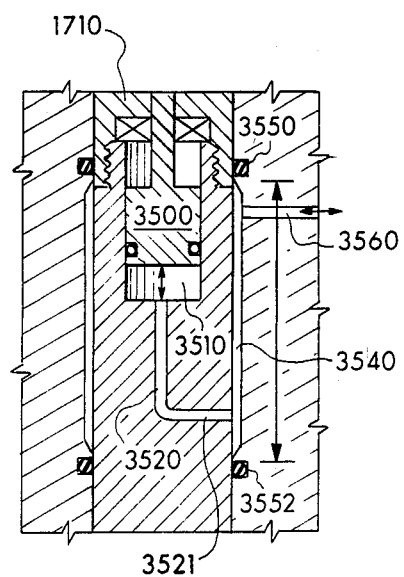
FIG. 36 is an illustration showing the operation of the embodiment of FIG. 35.

In this embodiment, the internal piston 1720 is modified as follows. The upper portion 2310 of the piston 1710 remains unchanged. However, the lower head portion, now designated 3500, takes on a different configuration as shown in FIG. 35. The lower head 3500 is simply a cylinder having an O-ring seal 3502 engaging the sidewalls of a chamber 3510. The chamber has a lower passageway 3520 which provides an outlet into chamber 3540. When piston assembly 1710 has been raised into the operating position with a core sample 210 in place in the sample holder 70, as shown in FIG. 2, then the port 3521 will be located, as shown in FIG. 36, between O-rings 3550 and 3552. Chamber 3540, which is formed by slightly enlarging the diameter of opening 1840 (see FIG. 19), permits gas communication from chamber 3510, via passageway 3520 and port 3521, to passageway 3560 and fitting 3562. By applying pressure to 3562 and through the above-mentioned passageway, piston 3500 is driven upward, causing piston head 2320 to seal at 2242. A gas pressure of about 125 psig is required to provide adequate sealing force. A vacuum applied to 3562 will cause 3500 to move downward, thereby creating a helium flow path at 2242 for a permeability measurement as discussed before. This results in a simpler construction for the internal piston 1720 then set forth in the first embodiment.

Chamber 1702 is interconnected through a fluid passageway 3522, either to a low pressure gas source (about 10 to 25 psig) or a vent to atmospheric pressure. Passageway 3522 serves the same function as passageway 1812 (see FIG. 29) in the previously described embodiment; i.e., when pressure is applied, piston assembly 1710 is driven downward. Conversely, when piston assembly is being driven upward by applying gas pressure through opening 1760 (FIG. 29), then gas from chamber 1702 (FIG. 35) must be vented through passageway 3522 to the atmosphere.

When assembly 1710 is being driven downward to remove a core sample from core holder 70, and when port 3521 falls below O-ring 3552, then pressure in chamber 1710 will activate piston 3500, driving it upward thereby causing head 2320 to seal at 2242. This is fortuitous and necessary, because otherwise, when ports 2230 fall below O-ring 3552, gas would leak through ports 2230, then into passageway 2240, and out through perforated plate 900 to the atmosphere. Thereby the downward movement of piston assembly 1710 might cease, because the majority of the volume of gas intended to drive the assembly 1710 downward would leak out as described above. However, activation of piston 3500 seals off any potential high volume leak. A felt washer 3570 is provided around the shaft 1720 to preclude any dust or grit that falls from the core sample from getting between piston 3500 and its confining cylindrical walls, 3501.

In summary, the method and apparatus of the present invention relates to a carousel containing a plurality of core samples wherein the carousel, in a first embodiment, is always rotatably positioned between the radial stress mechanism 70 and the axial stress mechanism 60 and, in a alternate embodiment, is selectively insertable between these mechanisms. In either event, the carousel is loaded with the core samples and then the apparatus of the present invention automatically positions each core sample over the lower piston 1710. The lower piston 1710 raises each sample out of the container by pneumatically activating the piston as discussed above. The lower piston 1710 then holds the raised core sample in the sample holder 70 to form a test chamber with a first predetermined pressure applied by the lower piston 1710. An overburden stress, including both axial and radial stresses from the two different sources (lower piston 1710 and sample holder 70) is simultaneously applied. A second piston 1720, located internal to the lower piston 1710 either seals the lower end of the core sample in order to conduct the porosity test or is deactivated to open the lower end in order to conduct the permeability test. The core sample is then lowered from the test chamber and the carousel is rotated so that the next successive core sample can be inserted. Of course, this procedure repeats until all of the core samples in the carousel have been tested.

While the apparatus and method of the present invention have been specifically disclosed above and in several embodiments, it is to be expressly understood that changes and modifications could be made thereto and that the present invention is of the scope set forth in the following claims.

I claim:

1. An apparatus for automatically determining the permeability and porosity for a plurality of core samples, said apparatus comprising:

means containing a predetermined number of containers for releasably carrying said plurality of core samples, wherein each container carries only one core sample, means located under one of said containers for automatically raising the core sample in said one container upwardly and out of said one container, means connected to said raising means, connected to said carrying means and located directly above said one container and said raising means for automatically holding said raised core sample in response to said raising of said core sample by said raising means, means in said holding means for automatically delivering a pressurized gas to the top end of said raised core sample in order to conduct said permeability and porosity tests, means in said raising means for automatically and selectively sealing the lower end of said raised core sample when said porosity test is being conducted, said sealing means being further capable of opening the aforesaid end of said raised core sample when said permeability test is being conducted, and means connected to said carrying means for automatically moving said carrying means to position the next successive container over said raising means upon the lowering of said raised core sample back into said one container, said moving means being capable of automatically moving said carrying means until all of said plurality of core samples have been tested.

2. An apparatus for automatically determining the permeability and porosity for a plurality of core samples, said core samples having cylindrical sides, said apparatus comprising:

means having a predetermined number of containers for releasably carrying said plurality of core samples, wherein each container carries only one core sample, means located under one of said containers for automatically raising the core sample contained in said one core container upwardly and out of said one core container, means connected to said raising means and further connected to said carrier means and located directly above said one core container and said raising means for automatically holding said raised core sample in response to said raising of said core sample by said raising means, said raising means being capable of maintaining said raised core sample in sealed engagement with said holding means and being further capable of applying an axial overburden stress on the ends of said raised core sample, said holding means being further capable of applying, simultaneously with the application of said axial overburden stress, a radial overburden stress around said cylindrical sides of said raised core sample, means in said holding and raising means for automatically conducting said permeability and porosity tests while said radial and axial overburden stresses are being applied, means in said raising means for automatically and selectively sealing the lower end of said raised core sample when said porosity test is being conducted, said sealing means being further capable of opening the aforesaid end of said raised core sample when said permeability test is being conducted, and means connected to said carrying means for automatically moving said carrying means to position the next successive container over said raising means upon the lowering of said raised core sample back into said one container, said moving means being capable of moving said carrier means until all of said plurality of core samples have been tested.

3. An apparatus for automatically determining the permeability and porosity for a plurality of core samples, said core samples having cylindrical sides, said apparatus comprising:

means containing a predetermined number of containers for releasably carrying said plurality of core samples, wherein each container carries only one core sample, means located under one of said containers for automatically raising the core sample in said one container upwardly and out of said one container, means connected to said raising means and further connected to said carrying means and located directly above said one container and said raising means for automatically holding said raised core sample in response to said raising of said core sample by said raising means, said raising means being capable of maintaining said raised core sample in sealed engagement with said holding means and being further capable of applying an axial overburden stress on the ends of said raised core sample, said holding means being further capable of applying, simultaneously with the application of said axial overburden stress, a radial overburden stress around said cylindrical sides of said raised core sample, means in said holding means for automatically delivering a pressurized gas to the top end of said raised core sample in order to conduct said permeability and porosity tests while said radial and axial overburden stresses are applied, means in said raising means for automatically and selectively sealing the lower end of said raised core sample when said porosity test is being conducted, said sealing means being further capable of opening the aforesaid end of said raised core sample when said permeability test is being conducted, and means connected to said carrying means for automatically moving said carrying means to position the next successive holder over said raising means upon the lowering of said raised core sample back into said one container, said moving means being capable of moving said carrying means until all of said plurality of core samples have been tested.

4. The apparatus of claim 3 wherein said carrying means comprises:

means connected to said raising means and to said moving means for rotating with respect to said raising means, and a carousel firmly connected to said rotating means, said carousel being circularly shaped with said predetermined number of containers oriented near the outer circumference of said carousel.

5. The apparatus of claim 4 further comprising:

a light source, a formed hole located near each said container on said carrier for extending light from said light source only when each said container is positioned over said raising means by said moving means, and means receptive of said extending light through said formed hole for generating an electrical signal when said container is over said raising means.

6. The apparatus of claim 4 wherein said carousel has a formed slot on each said container on the outer circumference of said carousel extending substantially the length of said container in order to aid in the manual loading of said plurality of core samples into said containers.

7. The apparatus of claim 3 wherein said carrying means can be selectively removed and inserted between said raising means and holding means.

8. The apparatus of claim 3 wherein said delivering means further comprises:
- a formed passageway in said holding means for extending pressurized gas to the upper end of said raised core, and
- a perforated end plug plate operatively engaging said formed passageway and the end of said core sample for uniformly distributing said gas into said raised core sample.

9. The apparatus of claim 3 wherein said holding means further comprises:
- an elastic sleeve for selectively engaging the sides of said raised core sample,
- a formed chamber substantially around said sleeve, and
- means for transmitting a pressurized fluid into said chamber in order to contract said sleeve around said raised core sample so that said radial overburden stress is applied, said transmitting means being further capable of transmitting a vacuum into said chamber when said raised core sample is lowered from said holding means by said raising means.

10. The apparatus of claim 9 wherein said elastic sleeve has its opposing top and bottom ends both compressed and stretch-deformed to provide a fluid seal so that said transmitted pressurized fluid and vacuum are confined to said chamber.

11. The apparatus of claim 3 wherein said raising means is capable of raising core samples within a predetermined range of heights.

12. The apparatus of claim 3 further comprising means operative with each said holder in said holding means for determining whether the core sample contained therein is above a predetermined minimum height.

13. The apparatus of claim 3 further comprising means connected to said holding means for sensing the presence of said raising means in said holding means.

14. An apparatus for automatically determining the permeability and porosity for a plurality of core samples, said apparatus comprising:
- means containing a predetermined number of containers for releasably carrying said plurality of core samples, wherein each container carries only one core sample,
- means located under one of said containers for raising the core sample in said one container upwardly and out of said one container,
- means connected to said raising means and further connected to said carrying means and located directly above said one container and said raising means for holding said raised core sample, said raising means being capable of maintaining said raised core sample in sealed engagement with said holding means and being further capable of applying an axial overburden stress on the ends of said raised core sample, said holding means being further capable of applying, simultaneously with the application of said axial overburden stress, a radial overburden stress around the cylindrical sides of said raised core sample,
- means in said holding means for delivering a pressurized gas to the top end of said raised core sample in order to conduct said permeability and porosity tests while said radial and axial overburden stresses are applied,
- means connected to said carrying means for moving said carrying means to position the next successive holder over said raising means upon the lowering of said raised core sample back into said one container, said moving means being capable of moving said carrying means until all of said plurality of core samples have been tested,
- a first formed passageway in said raising means for delivering pressurized gas,
- a first piston operatively responsive to said pressurized gas in said first passageway for upwardly lifting said core sample into said holding means, said first piston being capable of sealing said core sample in said holding means to form a test chamber for said raised core sample and for applying said axial overburden stress,
- a second formed passageway in said raising means for conveying pressurized gas,
- a second piston internal to said first piston and operatively responsive to the pressurized gas in said second formed passageway for selectively sealing the upper end of said first piston when said porosity test is being conducted and for opening the upper end of said first piston when said permeability test is being conducted, and
- means in fluid communication with said open end of said first piston for delivering gas from said permeability test from the bottom end of said core sample outwardly from said raising means.

15. An apparatus for automatically determining the permeability and porosity for a plurality of core samples of varying lengths within a predetermined range of lengths, said core samples having cylindrical sides, said apparatus comprising:
- means containing a predetermined number of containers for releasably carrying said plurality of core samples, wherein each container carries only one core sample,
- means located under one of said containers for automatically raising the core sample in said one container upwardly and out of said one container,
- means connected to said raising means, connected to said carrying means and located directly above said one container and said raising means for holding said raised core sample in response to said raising of said core samples by said raising means, said raising means being capable of maintaining said raised core sample in sealed engagement for each sample having a length within said predetermined range of lengths with said holding means to form a test chamber and being further capable of applying an axial overburden stress on the ends of said raised core sample, said holding means being further capable of applying a radial overburden stress around said cylindrical sides of said raised core sample,
- means in said holding means for automatically delivering a pressurized gas to the top end of said raised core sample in order to conduct said permeability and porosity tests while said radial and axial overburden stresses are applied, means internal to said raising means for automatically selectively sealing the upper end of said raising means when said porosity test is being conducted and for opening the upper end of said raising means when said permeability test is being conducted, means in fluid communication with said open end of said raising means for delivering gas from said permeability test from the bottom end of said core sample outwardly from said raising means, and means connected to said carrying means for automatically moving said carrying means to position the next successive holder over said raising means upon the lowering of said raised core sample back into said one container, said moving means being capable of moving said carrying means until all of said plurality of core samples have been tested.

16. The apparatus of claim 15 wherein said carrying means comprises:

means connected to said raising means and to said moving means for rotating with respect to said raising means, and a carousel firmly connected to said rotating means, said carousel being circularly shaped with said predetermined number of containers oriented near the outer circumference of said carousel.

17. The apparatus of claim 16 further comprising:
a light source,
a formed hole located near each said container on said carrier for extending light from said light source only when each said container is positioned over said raising means by said moving means, and
means receptive of said extended light through said formed hole for generating an electrical signal when said container is over said raising means.

18. The apparatus of claim 16 wherein said carousel has a formed slot on each said container on the outer circumference of said carousel extending substantially the length of said container in order to aid in the manual loading of said plurality of core samples into said containers.

19. The apparatus of claim 15 wherein said carrying means can be selectively removed and inserted between said raising means and holding means.

20. The apparatus of claim 15 wherein said delivering means further comprises:
a formed passageway in said holding means for extending pressurized gas to the upper end of said raised core, and
a perforated end plug plate operatively engaging said formed passageway and the end of said core sample for uniformly distributing said gas into said raised core sample.

21. The apparatus of claim 15 wherein said holding means further comprises:
an elastic sleeve for selectively engaging the sides of said raised core sample,
a formed chamber substantially around said sleeve, and
means for transmitting a pessurized fluid into said chamber in order to contract said sleeve around said raised core sample so that said radial overburden stress is applied, said transmitting means being further capable of transmitting a vacuum into said chamber when said raised core sample is lowered from said holding means by said raising means.

22. The apparatus of claim 21 wherein said elastic sleeve has its opposing top and bottom ends both compressed and stretch-deformed to provide a fluid seal so that said transmitted pressurized fluid and vacuum are confined to said chamber.

23. The apparatus of claim 15 further comprising means operative with each said holder in said holding means for determining whether the core sample contained therein is within said predetermined range of heights.

24. The apparatus of claim 15 further comprising means connected to said holding means for sensing the presence of said raising means in said holding means.

25. An apparatus for automatically determining the permeability and porosity for a plurality of core samples, wherein said core samples vary within a predetermined range of heights and said core samples have cylindrical sides, said apparatus comprising:

a carousel having an outer circumference, said carousel containing a predetermined number of containers located near said outer circumference of said carousel for releasably carrying said plurality of core samples, said carousel being further capable of being selectively removed and inserted from said apparatus, means located under one of said containers of said carousel for raising the core sample in said one container upwardly and out of said one container, means connected to said raising means, further connected to said carousel and located directly above said one container and said rising means for automatically holding said raised core sample, said raising means being capable of maintaining said raised core sample in sealed engagement with said holding means to form a test chamber and being further capable of applying an axial overburden stress on the ends of said raised core sample, said holding means being further capable of applying a radial overburden stress around said cylindrical sides of said raised core sample, means in said holding means for automatically delivering a pressurized gas to the top end of said raised core sample in order to conduct said permeability and porosity tests while said radial and axial overburden stresses are applied, first means internal to said raising means for selectively sealing the upper end of said raising means when said porosity test is being conducted and for opening the upper end of said raising means when said permeability test is being conducted, second means internal to said raising means and in fluid communication with said open end of said raising means for delivering as through the bottom end of said core sample and outwardly from said raising means during said permeability test, and means connected to said carousel for rotating said carousel to position the next successive container over said raising means upon the lowering of said raised core sample back into said one container, said rotating means being capable of rotating said carousel until all of said plurality of core samples have been tested.

26. The apparatus of claim 25 further comprising:
a light source,
a formed hole located near each said container on said carousel for extending light from said light source only when each said container is positioned over said raising means by said rotating means, and means receptive of said extended light through said formed hole for generating an electrical signal when said container is over said raising means.

27. The apparatus of claim 25 wherein said carousel has a formed slot on each said container on said outer circumference of said carousel extending substantially the length of said container in order to aid in the manual loading of said plurality of core samples into said containers.

28. The apparatus of claim 25 wherein said delivering means further comprises:
 a formed passageway in said holding means for extending pressurized gas to the upper end of said raised core, and
 a perforated end plug plate operatively engaging said formed passageway and the end of said core sample for uniformly distributing said gas into said raised core sample.

29. The apparatus of claim 25 wherein said holding means further comprises:
 an elastic sleeve for selectively engaging the sides of said raised core sample,
 a formed chamber substantially around said sleeve, and
 means for transmitting a pressurized fluid into said chamber in order to contract said sleeve around said raised core sample so that said radial overburden stress is applied, said transmitting means being further capable of transmitting a vacuum into said chamber when said raised core sample is lowered from said holding means by said raising means.

30. The apparatus of claim 29 wherein said elastic sleeve has its opposing top and bottom ends both compressed and stretch-deformed to provide a fluid seal so that said transmitted pressurized fluid and vacuum are confined to said chamber.

31. The apparatus of claim 25 further comprising means operative with each said container in said holding means for determining whether the core sample contained therein is above a predetermined minimum height.

32. The apparatus of claim 25 further comprising means connected to said holding means for sensing the presence of said raising means in said holding means.

33. A method of automatically conducting permeability and porosity tests on a plurality of core samples, said method comprising the steps of:
 (a) manually loading a plurality of core samples into a carousel having a container for each of said core samples,
 (b) automatically positioning a first core sample in a first container of said carousel over a piston,
 (c) automatically raising said first core sample out of said first container in response to the positioning of the first core sample over the piston by pneumatically activating said piston,
 (d) automatically holding said raised first core sample in a test chamber with said piston in response to the raising of the first core sample,
 (e) sealing said raised first core sample in said test chamber with a predetermined pressure applied by said piston,
 (f) simultaneously applying at least one set of (1) an axial stress with said piston to the ends of said first core sample and (2) a radial stress with an elastic sleeve located in said chamber around the sides of said first core sample in order to simulate an overburden stress and in response to the sealing of said raised first core sample in said test chamber,
 (g) automatically performing at least one set of said porosity and permeability tests on said first core sample in response to said application of the axial and radial stresses to said first core sample,
 (h) automatically lowering said first core sample from said test chamber upon completion of at least one set of said porosity and permeability tests conducted for at least one predetermined overburden stress, and
 automatically repeating steps (b) through (h) for each of the remaining loaded core samples by turning the carousel to position the next successive container over said piston.

34. A method of automatically conducting permeability and porosity tests on a plurality of core samples, said method comprising the steps of:
 (a) manually loading a plurality of core samples into a carousel having a container for each of said core samples,
 (b) automatically positioning a first core sample in a first container of said carousel over a piston,
 (c) automatically raising said first core sample out of said first container in response to the positioning of the first core sample over the piston by pneumatically activating said piston,
 (d) automatically holding said raised first core sample in a test chamber with said piston in response to the raising of the first core sample,
 (e) automatically sealing said raised first core sample in said test chamber with a predetermined pressure applied by said piston,
 (f) automatically applying an axial overburden stress with said piston to the ends of said first core sample,
 (g) automatically applying a radial overburden stress with an elastic sleeve located in said chamber around the sides of said first core sample,
 (h) automatically activating a second piston located internal to said first piston to seal the lower end of said first core sample in order to conduct said porosity test,
 (i) automatically deactivating said second piston to open the lower end of said sealed core sample in order to conduct said permeability test and in response to the completion of said porosity test,
 (j) automatically lowering said first core sample from said test chamber upon completion of at least one set of said porosity and permeability tests conducted for at least one predetermined overburden stress, and
 automatically repeating steps (b) through (j) for each of the remaining loaded core samples by turning the carousel to position the next successive container over said piston.

35. A method of automatically conducting permeability and porosity tests on a plurality of core samples, said method comprising the steps of:
 (a) manually loading a plurality of core samples into a carousel having a container for each of said core samples,
 (b) automatically positioning a first core sample in a first container of said carousel over a first piston,
 (c) automatically raising said first core sample out of said first container by pneumatically activating said first piston in response to the positioning of the first core sample over the piston, (d) automatically receiving said raised first core sample in a test chamber located directly above said first piston in response to the raising of the first core sample, (e) automatically sealing said raised first core sample in said test chamber with a predetermined stress applied by said first piston, (f) simultaneously and automatically applying at least one set of (1) an axial overburden stress with said first piston to the ends of said first core sample and (2) a radial stress with an elastic sleeve located in said chamber around the sides of said first core sample in order to simulate an overburden stress, (g) activating a second piston located internal to said first piston to maintain the seal over the lower end of said first core sample when conducting at least one said porosity test, (h) deactivating said second piston to open the lower end of said sealed core sample when conducting at least one said permeability test, (i) automatically lowering said first core sample from said test chamber upon completion of at least one set of said porosity and permeability tests conducted for at least one predetermined overburden stress, and automatically repeating steps (b) through (j) for each of the remaining loaded core samples by turning the carousel to position the next successive container over said piston.

36. A method of conducting permeability and porosity tests on a plurality of core samples of varying lengths within a predetermined range with an apparatus having a test chamber, said method comprising the steps of:

(a) manually loading a plurality of core samples into at least one carousel having a container for each of said core samples, (b) manually inserting said at least one carousel into the apparatus, said method further comprising the automatic steps of:

(1) positioning a first core sample in a first container of said carousel over a piston, (2) raising said first core sample out of said first container by pneumatically activating said piston in response to said positioning, (3) holding said raised first core sample in a test chamber with said piston in response to said raising, (4) sealing said raised first core sample in said test chamber with a predetermined pressure applied by said piston in response to said holding, (5) simultaneously applying (1) an axial overburden stress with said piston to the ends of said first core sample and (2) a radial stress with an elastic sleeve located in said chamber around the sides of said first core sample in order to simulate an overburden stress in response to said sealing, (6) activating a second piston located internal to said first piston to seal the lower end of said first core sample when conducting said permeability test, (7) deactivating said second piston to open the lower end of said sealed core sample when conducting said permeability test, (8) repeating steps (5), (6), and (7) for different overburden stresses, (9) lowering said first core sample from said test chamber upon completion of at least one set of said porosity and permeability tests conducted for at least one predetermined overburden stress, and automatically repeating steps (1) through (8) for each of the remaining loaded core samples by turning said at least one carousel to position the next successive container over said piston.

* * * * *

UNITED STATES PATENT AND TRADEMARK OFFICE
CERTIFICATE OF CORRECTION

PATENT NO. : 4,573,342

DATED : March 4, 1986

INVENTOR(S) : Stanley C. Jones

It is certified that error appears in the above-identified patent and that said Letters Patent are hereby corrected as shown below:

Col. 6, line 59:  Delete "edge" and insert --ledge--.
Col. 7, line 53:  Delete "700" and insert --600-.
Col. 8, line 31:  Delete "Fig. ." and insert --Fig. 2.--.
Col. 8, line 32:  Delete "pr itted" and insert --press-fitted--.
Col. 13, line 45: Delete "passagewy" and insert --passageway--.
Col. 14, line 16: Delete "passageways" and insert --passageway--.

Signed and Sealed this

Third Day of June 1986

[SEAL]

Attest:

Attesting Officer

DONALD J. QUIGG

Commissioner of Patents and Trademarks